(12) United States Patent
Bech et al.

(10) Patent No.: US 6,190,879 B1
(45) Date of Patent: Feb. 20, 2001

(54) MICROBIAL TRANSGLUTAMINASES, THEIR PRODUCTION AND USE

(75) Inventors: Lisbeth Bech, Hillerød; Iben Angelica Nørrevang, Allerød; Torben Halkier, Birkerød; Grethe Rasmussen, København, all of (DK); Thomas Schäfer, Farum (DE); Jens Tønne Andersen, Nærum (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/294,565

(22) Filed: Apr. 20, 1999

Related U.S. Application Data

(63) Continuation of application No. 08/793,426, filed on Feb. 25, 1997, now Pat. No. 6,100,053.

(30) Foreign Application Priority Data

Aug. 26, 1994 (DK) .................................... 0990/94
Aug. 24, 1995 (DK) .................................... 0947/95

(51) Int. Cl.⁷ .............................. C12P 21/06; C12N 9/10; A23G 1/05
(52) U.S. Cl. .................. 435/68.1; 435/72.1; 435/193; 426/573
(58) Field of Search ................. 435/68.1, 71.2, 435/193, 227; 426/573

(56) References Cited

U.S. PATENT DOCUMENTS 5,156,956  10/1992  Motoki et al. ............ 435/68.1
5,252,469  10/1993  Andou et al. ............ 435/71.2

FOREIGN PATENT DOCUMENTS

74789/91  5/1991  (AU) .
0379606  8/1990  (EP) .
0481504  4/1992  (EP) .
127471  1/1989  (JP) .
4108381  4/1992  (JP) .
678783  3/1994  (JP) .

OTHER PUBLICATIONS

Cutis et al. (1976) in Methods in Enzymology, vol. XLV, Ed. Lorand, pp. 177–191.*
Klein, et al., Chemical Abstracts, vol. 116, No. 23, Abstract No. 230570d (1992).
Geneseq Database accession No. Q24197.
Geneseq Database accession No. Q24201.
Hiroyasu, et al., Chemical Abstracts, vol. 117, No. 9, Abstract No. 88752q (Aug. 31, 1992).
Masao, et al., Chemical Abstracts, vol. 112, No. 1, Abstract No. 6095n (Jan. 1, 1990).
Yoko, et al., Chemical Abstracts, vol. 121, No. 5, Abstract No. 56249x (Aug. 1, 1994).
Lorand, et al., Analytical Biochemistry, vol. 50, pp. 623–631 (1972).
Ochi, et al, Int'l Journal Of Systematic Bacteriology, vol. 44, No. 2, pp. 285–292 (Apr. 1994).
Williams, et al., Journal of General Microbiology, vol. 129, pp. 1743–1813 (1983).
Washizu, et al., Biosci Biotech, Biochem, vol. 58 No. 1, pp. 82–87 (1994).
Kampfer, et al., Journal of General Microbiology, vol. 137 pp. 1831–1891 (1991).

* cited by examiner

*Primary Examiner*—Elizabeth Slobodyansky
(74) *Attorney, Agent, or Firm*—Elias J. Lambiris; Reza Green

(57) ABSTRACT

A method for identifying a transglutaminase-producing microorganism based on a selective assay is disclosed.

8 Claims, 3 Drawing Sheets

US 6,190,879 B1

MICROBIAL TRANSGLUTAMINASES, THEIR PRODUCTION AND USE

CROSS-REFERENCE TO RELATED APPLICATIONS

This application is a continuation of U.S. application Ser. No. 08/793,426 filed Feb. 25, 1997, now U.S. Pat. No. 6,100,053, which is a 35 U.S.C. 371 national application of PCT/DK95/00347 filed Aug. 28, 1995 and claims priority under 35 U.S.C. 119 of Danish applications 0990/94 filed Aug. 26, 1994 and 0947/95 filed Aug. 24, 1995, the contents of which are fully incorporated herein by reference.

The present invention relates to microbial transglutaminases, a DNA construct encoding a transglutaminase, a method of producing the transglutaminases, a composition comprising the transglutaminase and a method for producing a gel or protein gelation composition; and the use thereof.

BACKGROUND OF THE INVENTION

Transglutaminases (EC 2.3.2.13) are enzymes capable of catalyzing an acyl transfer reaction in which a γ-carboxyamide group of a peptide bound glutamine residue is the acyl donor. Primary amino groups in a variety of compounds may function as acyl acceptors with the subsequent formation of monosubstituted γ-amides of peptide bound glutamic acid. When the ε-amino group of a lysine residue in a peptide chain serves as the acyl acceptor, the transglutaminases form intramolecular or intermolecular γ-glutamyl-ε-lysyl crosslinks.

This peptide crosslinking activity has shown useful for a variety of industrial purposes, including gelling of proteins, improvement of baking quality of flour, producing paste type food materia from protein, fat and water, preparation of cheese from milk concentrate, binding of chopped meat product, improvement of taste and texture of food proteins, casein finishing in leather processing etc.

A wide array of transglutaminases have been identified and characterized from a number of animals and a few plant species. The most widely used animal derived transglutaminase, FXIIIa, is a $Ca^{2+}$-dependent multi-subunit enzyme which is product inhibited, properties which are a disadvantage for many industrial applications and for production. A $Ca^{2+}$-dependent transglutaminase from the slime mould *Physarum polycephalum* has been described in Klein et al., (1992).

Only few microbial transglutaminases have been disclosed, namely tranglutaminases from the species *Streptoverticillium mobaraense, Streptoverticillium cinnamoneum,* and *Streptoverticillium griseocarneum* (in U.S. Pat. No. 5,156,956) and from the species contemplated to be *Streptomyces lavendulae* (in U.S. Pat. No. 5,252,469).

U.S. Pat. No. 5,156,956 discloses that, after an extensive search for transglutaminases including screening a wide range of organisms and more than 5000 isolates of microbial origin, only the above-mentioned three Streptoverticillium species were found to produce transglutaminase. Members of this former genus *Streptoverticillium* are now generally included within the genus *Streptomyces* (Kaempfer et al. (1991), and Ochi et al. (1994)).

U.S. Pat. No. 5,252,469 discloses transglutaminase from what was believed to be two related species: Streptomyces sp., and *Streptomyces lavendulae*. However, from the disclosed data for the contemplated *S. lavendulae* strain it is evident to the skilled person that the disclosed strain is not *S. lavendulae*.

Streptoverticillia are classified together in Cluster group F (clusters 55 to 67) of Streptomyces and related genera (Williams et al.). Therefore the known microbial transglutaminases all originate from members of this Cluster group as defined in Williams et al. *Streptomyces lavendulae* is also classified in Cluster group F.

All known microbial transglutaminases have been identified by using a conventional enzyme assay in which hydroxylamine is converted to hydroxamic acid (Folk, J. E. & Cole, P. W. (1966)).

In order to construct strains overproducing different enzymes, recombinant DNA techniques are widely used. For the same purpose, the *Streptoverticillium mobaraense* transglutaminase gene has been cloned for expression in *Escherichia coli, Streptomyces lividans,* and *Saccharomyces cerevisiae* (Washizu et al., Tahekana et al., and EP-A-0 481 504). Even the most succesful of these approaches (Washizu et al.) resulted in a production yield much lower than the yield in the wildtype *S. mobaraense* strain, in spite of extensive experimentation and optimization. Thus, none of the efforts to overproduce the *S. mobaraense* enzyme have been successful, although they included a number of different approaches such as chemical synthesis of a codon-optimized gene and its subsequent expression (as a cleavable heterologous signal peptide fusion to the mature transglutaminase) to the periplasm of *E. coli*; or expression as a similar fusion to the mature transglutaminase in *S. cerevisiae*; or expression as a similar fusion to pro-transglutaminase in *S. cerevisiae*; or traditional isolation and expression of the natural DNA sequence encoding the pre-proenzyme in *S. lividans*.

U.S. Pat. No. 5,252,469 discloses strains closely related to *S. mobaraense* which produce higher amounts of transglutaminase by conventional techniques.

The object of the invention is to provide novel microbially derived transglutaminases, preferably in single-component or mono-component form, a novel gene encoding a transglutaminase, and a method for producing the transglutaminase in a better yield and higher purity than hitherto possible by recombinant DNA technology, as well as the use of the transglutaminase either alone or in combination with other enzymes for the use in a variety of industrial purposes, including gelling of proteins; improvement of baking quality of flour; producing paste type food or food ingredients from protein, fat and water; preparation of cheese from milk concentrate; binding of chopped meat or fish products; improvement of taste and texture of food proteins; casein finishing in leather processing; shoe shine, etc.

SUMMARY OF THE INVENTION

It has been found that, by screening a wide array of bacterial and fungal strains, often screening of the same extract which in the traditional hydroxamate assay gave rise to a negative result, in a modified putrescine assay resulted in a positive reaction. Accordingly, the modified version of the putrescine incorporation assay was applied in a screening procedure which surprisingly resulted in detection of transglutaminase activity in a wide array of organisms.

Therefore, and opposite to what has hitherto been known, it has now been found that transglutaminases (TGases) are produced by an overwhelming array of phylogenetically dispersed microorganisms. Also, it has been found that even within Cluster groups other than Cluster group F, e.g. Cluster groups A and G, members have been found which produce transglutaminases.

Several of the provided enzymes may be useful for industrial applications. The industrial potential is underlined by three circumstances:

1. The novel transglutaminases of the invention may be obtained in the higher production yields than obtained for any other microbial transglutaminase;
2. A number of the TGase-producing strains provided by the mentioned assay are closely related to industrial production strains in current use, and can hence be subjected to recombinant DNA expression in closely related species; e.g. members of the genera Bacillus, Streptomyces, Aspergillus, and Trichoderma;
3. The novel transglutaminases of the invention may be found extracellularly.

By applying a number of different growth conditions for the organisms to be screened, the inventors also surprisingly found that these conditions, in several instances, were decisive for detection of TGase activity in the extract.

The inventors also succeeded in isolating and characterizing a DNA sequence from a strain of *Streptomyces lydicus*, exhibiting transglutaminase activity, thereby making it possible to prepare a single-component transglutaminase.

Accordingly, in another aspect the invention relates to a DNA construct comprising a DNA sequence encoding an enzyme exhibiting transglutaminase activity, which DNA sequence comprises
a) the DNA sequence shown in SEQ ID No. 1, and/or the DNA sequence obtainable from the plasmid in *E. coli* DSM 10175, or
b) an analogue of the DNA sequence shown in SEQ ID No. 1 and/or the DNA sequence obtainable from the plasmid in *E. coli* DSM 10175, which
   i) is at least 80% homologous with the DNA sequence shown in SEQ ID No. 1 and/or the DNA sequence obtainable from the plasmid in *E. coli* DSM 10175, or
   ii) encodes a polypeptide which is at least 79% homologous with the polypeptide encoded by a DNA sequence comprising the DNA sequence shown in SEQ ID No. 1 and/or the DNA sequence obtainable from the plasmid in *E. coli* DSM 10175, or
   iii) encodes a polypeptide which is immunologically reactive with an antibody raised against the purified transglutaminase encoded by the DNA sequence shown in SEQ ID No 1 and/or obtainable from the plasmid in *E. coli*, DSM 10175.

It is believed that the DNA sequence shown in SEQ ID No. 1 is identical to the DNA sequence obtainable from the plasmid in *E. coli*, DSM 10175.

The strain *E. coli* was deposited under the deposition number DSM 10175 on Aug. 23, 1995 at the DSM—Deutsche Sammlung von Mikroorganismen und Zellkulturen GmbH, Maascheroder Weg 1b, D-38125 Braunschweig, Germany, according to the Budapest Treaty.

In a further aspect, the invention relates to a method for the production of transglutaminase comprising cultivation in a suitable nutrient medium a strain belonging to any of the classes, orders, families, genera and species specified in the specification, examples and claims herein, especially *Streptomyces lydicus*, NRRL B-3446.

The invention further relates to a transglutaminase composition comprising the transglutaminase preparation of the present invention and a stabilizer.

In yet another aspect, the invention relates to a method of crosslinking proteins wherein a transglutaminase composition comprising the transglutaminase preparation of the present invention is contacted with a proteinaceous substrate.

Further, the present invention relates to use of the transglutaminase preparation of the present invention in flour, meat products, fish products, cosmetics, cheese, milk products, gelled food products and shoe shine.

DETAILED DESCRIPTION OF THE INVENTION

Figure 1:
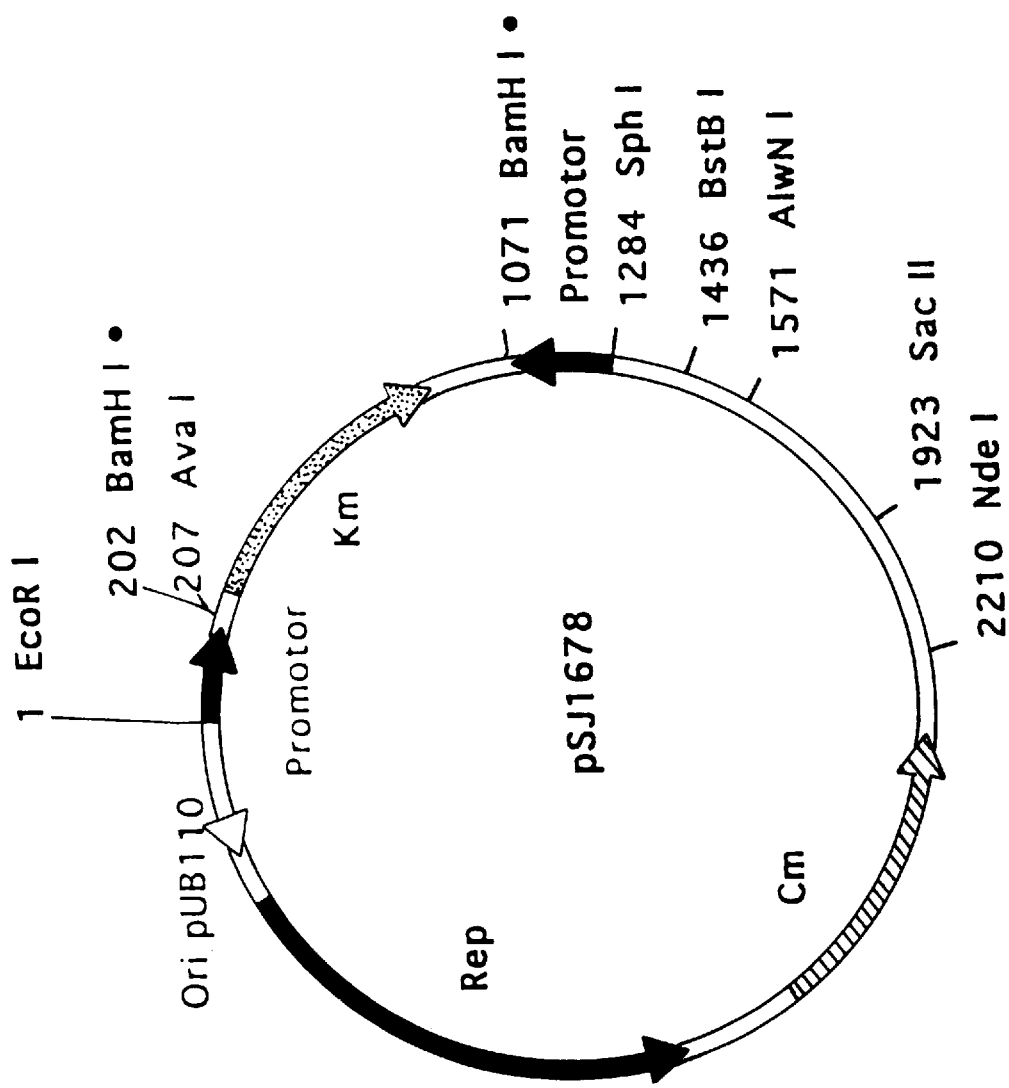
FIG. 1 is a schematic representation of a plasmid designated pSJ1678.

In the present specification and claims, the term "transglutaminase" is intended to be understood as an enzyme capable of catalyzing an acyl transfer reaction in which a gamma-carboxyamide group of a peptide-bound glutamine residue is the acyl donor. The term "$Ca^{2+}$-independent transglutaminase" is intended to be understood as a transglutaminase active in the absence of $Ca^{2+}$-ions, i.e. in the presence of excess EDTA.

The transglutaminase may be a component occurring in an enzyme system produced by a given microorganism, such an enzyme system mostly comprising several different enzyme components. Alternatively, the transglutaminase may be a single component, i.e. a component essentially free of other enzyme components usually occurring in an enzyme system produced by a given microorganism, the single component being a recombinant component, i.e. produced by cloning of a DNA sequence encoding the single component and subsequent cell transformed with the DNA sequence and expressed in a host. The host is preferably a heterologous host, but the host may under certain conditions also be the homologous host.

The native or unmodified transglutaminase may be of microbial origin.

It is contemplated that transglutaminases may be obtainable by or derived from a fungus, a bacterium or from yeast. The derived enzyme component may be either homologous or heterologous component. Preferably, the component is homologous. However, a heterologous component which is immunologically reactive with an antibody raised against a highly purified transglutaminase and which is derived from a specific microorganism is also preferred.

In the present context the term "derivable" or "derived from" is intended not only to indicate a transglutaminase produced by a strain of the organism in question, but also a transglutaminase encoded by a DNA sequence isolated from such strain and produced in a host organism transformed with said DNA sequence. Furthermore, the term is intended to indicate a transglutaminase which is encoded by a DNA sequence of synthetic and/or cDNA origin and which has the identifying characteristics of the transglutaminase in question.

In a preferred embodiment, the invention relates to transglutaminase preparation which is producible by cultivation of a fungus, preferably a fungus which belongs to basidiomycotina, ascomycotina or zygomycotina.

Examples of useful basidiomycotina are strains belonging to the group consisting of the orders Agaricales, Aphyllophorales, Ceratobasidiales, Auriculaariales and Nidulariales, or strains belonging to the group consisting of the families Tricholomataceae, Amanitaceae, Agaricaceae, Strophariaceae, Coprinaceae, Cortinariaceae, Paxillaceae, Polyporaceae, Coriolaceae, Fomitopsidaceae, Stereaceae, Hymenochaetaceae, Lachnocladiaceae, Ceratobasidiaceae, Auriculariaceae and Nidulariaceae, or strains belonging to the group consisting of the genera Tricholoma, Lyophyllum, Armillaria, Amanita, Agaricus, Chamaemyces, Stropharia, Hypholoma, Kuhneromyces, Pholiota, Coprinus, Psathyrella, Panaeolus, Gymnopilus, Hygrophoropsis, Pleurotus, Pycnoporus, Antrodia, Trametes, Amylostereum, Hymenochaete, Scytinostroma, Rhizoctonia, Auricularia and Nidula.

Preferred strains are those belonging to the species *Tricholoma flavovirens* or *Tricholoma myomyces,* Lyophyllum sp., Armillaria sp., *Amanita virosa,* Agaricus sp., *Chamaemyces fracidus, Stropharia coerulea, Hypholoma fasciculare, Kuhneromyces variabilis, Pholiota jahnii, Coprinus cinereus,* Coprinus sp., *Psathyrella condolleana, Panaeolus papilionaceus, Gymnopilus junonius, Hygrophoropsis aurantiaca, Pleurotus dryinus,* Pleurotus sp., *Pycnoporus cinnabarinus, Antrodia serialis, Trametes hirsuta, Amylostereum chailletii, Hymenochaete corticola, Scytinostroma portentosum, Rhizoctonia solani, Auricularia polytricha* and Nidula sp.

Especially useful examples are those strains belonging to the group consisting of the species Armillaria sp., CBS 372.94; *Coprinus cinereus,* IFO 30116; *Psathyrella condolleana,* CBS 628.95; *Panaeolus papilionaceus,* CBS 630.95; *Amylostereum chailletii,* CBS 373.94; and *Hymenochaete corticola,* CBS 371.94.

Examples of useful ascomycotina are strains belonging to the classes Discomycetes, Pyrenomycetes, Loculoascomycetes, and Plectomycetes, preferably those belonging to the orders Leotiales, Xylariales, Diaporthales, Sordariales, Halosphaeriales, Hypocreales, Dothideales, Eurotiales, and certain Ascomycetes of unknown order.

Preferred strains are strains belonging to the families Leotiaceae, Xylariaceae, Amphisphaeriaceae, Valsaceae, Chaetomiaceae, Lasiosphaeriaceae, Halosphaeriaceae, Hypocreaceae, Pleosporaceae, Mycosphaerellaceae, Botryosphaeriaceae, Sporormiaceae, Herpotrichiellaceae, and Trichocomataceae; especially strains belonging to the genera Dimorphosporum, Xylaria, Ascotricha, Nodulisporium, Savoryella, Valsa, Chaetomium, Podospora, Halosphaeriopsis, Lulworthia, Lignincola, Fusarium, Myrothecium, Trichoderma, Alternaria, Cochliobolus, Curvularia, Cercospora, Cladosporium, Botryosphaeria, Sporormiella, Preussia, Carponia, Coniothyrium, Byssochlamys, Talaromyces, Neosartorya, Warcupiella, Aspergillus, Beauveria, Hortea, Humicola, Monodictys and Dendryphiella.

Preferred are the species *Dimorphosporum disporatrichum,* Xylaria sp., *Ascotricha erinacea,* Nodulisporium sp., *Savoryella lignicola, Valsa pini, Chaetomium funicolum, Podospora tetraspora, Halosphaeriopsis mediosetigera, Lulworthia uniseptata,* Lignincola sp., *Fusarium armeniacum, Fusarium decemcellulare, Fusarium dimerum, Fusarium merismoides, Fusarium redolens, Fusarium flocciferum, Myrothecium roridum, Trichoderma harzianum, Alternaria alternata, Cochliobolus sativus, Curvularia borreiae, Cercospora beticola, Cercospora carisis, Cercospora fusimaculans, Cercospora hayi, Cercospora sesami, Cercospora traversiana, Cladosporium cladosporiodes, Cladosporium resinae, Cladosporium oxysporum, Cladosporium sphaeospermum, Botryosphaeria rhodina, Sporormiella australis, Sporormiella minima, Preussia isomera, Carponia solliomaris, Coniothyrium cerealis, Byssochlamys fulva, Talaromyces helicus, Neosartorya quadricineta, Warcupiella spinulosa, Aspergillus foetidus, Aspergillus giganteus, Aspergillus heteromorphus, Aspergillus puniceus, Aspergillus tamarli, Beauveria cylindrospora, Beauveria calendonica, Hortea werneckii, Humicola alopallonella, Monodictys pelagica* and *Dendryphiella salina.*

Especially preferred are the species *Dimorphosporum disporatrichum,* ATCC 24562; *Savoryella lignicola,* CBS 626.95; *Chaetomium funicolum,* ATCC 42779; *Lulworthia uniseptata,* IFO 32137; *Fusarium armeniacum,* IBT 2173; *Fusarium decemcellulare,* CBS 315.73; *Fusarium dimerum,* IBT 1796; *Fusarium merismoides,* ATCC 16561; *Fusarium redolens,* IBT 2058; *Myrothecium roridum,* ATCC 20605; *Trichoderma harzianum,* CBS 223.93; *Alternaria alternata,* CBS 448.94; *Curvularia borreiae,* CBS 859.73; *Cercospora beticola,* ATCC 28056; *Cercospora carisis,* IMI 167.425; *Cercospora fusimaculans,* IMI 167.426; *Cercospora hayi,* IMI 160.414; *Cercospora sesami,* IMI 318.913; *Cercospora traversiana,* IMI 318.080; *Cladosporium resinae,* CBS 174.61; *Cladosporium sphaeospermum,* CBS 444.94; *Byssochlamys fulva,* AHU 9252; *Talaromyces helicus,* ATCC 10451; *Neosartorya quadricineta,* IBT 11057; *Warcupiella spinulosa,* NKBC 1495; *Aspergillus foetidus,* CBS 565.65; *Aspergillus giganteus,* CBS 526.65; *Aspergillus heteromorphus,* CBS 117.55; *Aspergillus puniceus,* IAM 13893; *Aspergillus tamarii,* IBT 3824; *Beauveria cylindrospora,* CBS 719.70; *Beauveria calendonica,* CBS 485.88; *Hortea werneckii,* CBS 446.94; *Monodictys pelagica,* CBS 625.95; and *Dendryphiella salina,* CBS 447.94.

Examples of useful zygomycota are strains belonging to the order Mucorales, preferably strains belonging to the genera Mucor and Cunninghamella.

Preferred species are *Mucor aligarensis,* preferably ATCC 28928, *Mucor luteus* and *Cunninghamella elegans,* preferably AHU 9445.

As shown in the examples below, the fungal transglutaminase preparations of the invention are capable of polymerizing α-casein, also a relatively high temperature, i.e. at temperatures where the enzyme activity is at optimum.

Preferred fungal transglutaminase preparations of the invention exhibit optimum activity at a temperature of at least 55° C., preferably at least 60° C., more preferably at least 70° C. even more preferably at least 80° C., especially at least 90° C. Such preparations are for example producible by cultivation of strains belonging to the genera Savoryella, Cladosporium, Monodictys, Hymenochaete and Lulworthia, especially strains belonging to the species *Savoryella lignicola, Cladosporium sphaeospermum, Hymenochaete corticola, Monodictys pelagica* and *Lulworthia uniseptata.*

Other preferred fungal transglutaminase preparations of the invention exhibit optimum relative activity at a pH of at least 8.5, preferably at least 9.0. Such preparations are for example producible by cultivation of a strain belonging to the genera Savoryella, Cladosporium, Cercospora, Hymenochaete, Monodictys and Lulworthia.

Further, it is contemplated that the fungal transglutaminase activity is inhibited by phenylmethylsulfonylfluoride (PMSF).

Transglutaminases in general are thought to contain a cysteine-residue in the active site that is essential for catalysis. This is based upon the observation that compounds that react with free thiol-groups inhibit transglutaminases. These compounds are e.g. mono-iodoacetic acid or mercuri salts.

Transglutaminases inhibited by other types of compounds could have different catalytic mechanisms and thus differentiate the transglutaminases into groups analogous to the classification of the proteases. The four classes of proteases are distinguished based upon their inhibition by different compounds. For example the serine proteases are typically inhibited by phenylmethylsulfonylfluoride (PMSF) whereas the cysteine proteases are inhibited by the same compounds that inhibit transglutaminases.

In another aspect, the invention relates to a novel transglutaminase preparation which is producible by cultivation of a bacterium which, in contrast to the known microbial transglutaminases, does not belong to Cluster F of Streptomyces and related genera.

Preferred bacteria are gram-negative or gram-positive.

Examples of transglutaminase-producing gram-negative bacteria are strains belonging to the genera Pseudomonas, Hafnia, Hydrogenophaga, and Zymomonas.

Preferred examples of TGase-producing gram-negative bacteria are strains belonging to the species *Pseudomonas putida, Pseudomonas putida, Pseudomonas amyloderamosa, Hafnia alvei, Hydrogenophaga palleroni* (Basonym: *Pseudomonas palleroni*), Moo5A10 and *Zymomonas mobilis;* especially *Pseudomonas putida,* DSM 1693; *Pseudomonas putida,* NCIMB 9869; *Pseudomonas amyloderamosa,* ATCC 21262; *Hafnia alvei,* DSM 30163; *Hydrogenophaga palleroni,* DSM 63; Moo5A10, DSM 10094, and *Zymomonas mobilis,* DSM 424.

Examples of TG-ase-producing gram-positive bacteria are strains belonging to the genera Streptomyces, Rothia, Bacillus, Kitasatoa and Bacteridium.

Preferred examples of TGase-producing gram-positive bacteria are strains belonging to the species *Streptomyces lydicus, Streptomyces nigrescens, Streptomyces sioyaensis, Streptomyces platensis, Rothia dentocariosa, Bacillus badius, Bacillus mycoides, Bacillus firmus, Bacillus aneurinolyticus, Bacillus megaterium,* Bacillus sp., *B. amyloliquefaciens, Kitasatao purpurea,* Bacteridium sp. and *Bacillus megaterium.*

Most preferred are the strains *Streptomyces lydicus,* DSM 40555 and NRRL B-3446; *Streptomyces nigrescens,* ATCC 23941;*Streptomyces sioyaensis,* ATCC 13989; *Streptomyces platensis,* DSM 40041; *Bacillus badius,* DSM 23; *Bacillus mycoides,* GJB 371; *Bacillus firmus,* ATCC 17060; *Bacillus firmus,* DSM 12; *Bacillus aneurinolyticus,* ATCC 12856; *Bacillus megaterium,* ATCC 13632; *Bacillus megaterium,* ATCC 15450; *Bacillus megaterium,* AJ 3355 and Ferm-P 1201; Bacillus sp., ATCC 21537; *B. Amyloliquefaciens,* ATCC 23843; *Kitasatao purpurea,* DSM 43362; Bacteridium sp.DSM 10093, Bacteridium sp., CBS 495.74.

Preferred bacterial transglutaminase preparations of the invention exhibit optimum activity at a pH of at least 6.5, preferably at least 7.0, more preferably at least 7.5, even more preferably at least 8.0, especially at least 8.5, most preferably at least 9.0.

Further, the transglutaminase activity of preferred bacterial transglutaminase preparations of the invention is inhibited by phenylmethylsulfonylfluoride (PMSF), see example 16.

Preferably, the transglutaminase is a recombinant transglutaminase, i.e. a transglutaminase essentially free from other proteins or enzyme proteins from the parent microorganism. A recombinant transglutaminase may be cloned and expressed according to standard techniques conventional to the skilled person.

Advantageously, a parent transglutaminase of bacterial origin may be used, e.g. a transglutaminase derivable from a strain of the genus Streptomyces, Actinoplanes, Amorphosporangium, Amycolata, Dactolosporangium, Bacteridium, Kitasatoa, Micronospora, or Bacillus. For instance, the parent transglutaminase may be derivable from a strain of the species *Streptomyces lydicus* (deposited at ARS Patent Culture Collection North Central Region, 1815 North University Street, Peonia, Ill. 61604, U.S.A., NRLL B-3446 (former *Streptomyces libani*).

In a preferred embodiment, the parent transglutaminase is a *Streptomyces lydicus,* NRRL B-3446, transglutaminase, or is a functional analogue of said parent transglutaminases which i) comprises an amino acid sequence being at least 60% homologous with the amino acid sequence of the parent transglutaminase, ii) reacts with an antibody raised against the parent transglutaminase, and/or iii) is encoded by a DNA sequence which hybridizes with the same probe as a DNA sequence encoding the parent transglutaminase.

Property i) of the analogue is intended to indicate the degree of identity between the analogue and the parent transglutaminase indicating a derivation of the first sequence from the second. In particular, a polypeptide is considered to be homologous to the parent transglutaminase if a comparison of the respective amino acid sequences reveals an identity of greater than about 60%, such as above 70%, 80%, 85%, 90% or even 95%. Sequence comparisons can be performed via known algorithms, such as the one described by Lipman and Pearson (1985).

The additional properties ii) and iii) of the analogue of the parent transglutaminase may be determined as follows:

Property ii), i.e. the immunological cross reactivity, may be assayed using an antibody raised against or reactive with at least one epitope of the parent transglutaminase. The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989.

The probe used in the characterization of the analogue in accordance with property iii) defined above, may suitably be prepared on the basis of the full or partial nucleotide or amino acid sequence of the parent transglutaminase. The hybridization may be carried out under any suitable conditions allowing the DNA sequences to hybridize. For instance, such conditions are hybridization under specified conditions, e.g. involving presoaking in 5×SSC and prehybridizing for 1 h at ~40° C. in a solution of 20% formamide, 5×Denhardt's solution, 50 mM sodium phosphate, pH 6.8, and 50 µg of denatured sonicated calf thymus DNA, followed by hybridization in the same solution supplemented with 100 µM ATP for 18 h at ~40° C., or other methods described by e.g. Sambrook et al., 1989.

Other examples of parent transglutaminases are those derived from or producible by *Streptomyces platentsis,* preferably DSM 40041, *Streptomyces nigrescens,* preferably TCC 23941, or *Streptomyces sioyaensis,* preferably ATCC 13989.

These parent transglutaminase are capable of polymerizing α-casein and are thus useful for many industrial purposes.

In a further aspect, the invention relates to a method for the production of transglutaminase comprising cultivation in a suitable nutrient medium a strain belonging to any of the classes, orders, families, genera and species specified herein, especially *Streptomyces lydicus,* NRRL B-3446.

In yet a further aspect, the invention relates to a transglutaminase composition comprising a fungal or bacterial transglutaminase preparation as described above and a stabilizer.

The invention also relates to a method of crosslinking proteins wherein a transglutaminase composition comprising the fungal or bacterial transglutaminase preparation of the present invention is contacted with a proteinaceous substrate.

The transglutaminase preparation of the invention is useful in flour, meat products, fish products, cosmetics, cheese, milk products, gelled food products and shoe shine.

In the present context, the "analogue" of the DNA sequence shown in SEQ ID No. 1 is intended to indicate any DNA sequence encoding an enzyme exhibiting transglutaminase activity, which has any or all of the properties i)–iii). The analogous DNA sequence a) may be isolated from another or related (e.g. the same) organism producing the enzyme with transglutaminase activity on the basis of the DNA sequence shown in SEQ ID No. 1, e.g. using the procedures described herein, and thus, e.g. be an allelic or species variant of the DNA sequence comprising the DNA sequences shown herein, b) may be constructed on the basis of the DNA sequences shown in SEQ ID No. 1, e.g. by introduction of nucleotide substitutions which do not give rise to another amino acid sequence of the transglutaminase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al. (1991). Examples of conservative substitutions are within the group of basic amino acids (such as arginine, lysine, histidine), acidic amino acids (such as glutamic acid and aspartic acid), polar amino acids (such as cysteine, glutamine and asparagine), hydrophobic amino acids (such as proline, leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, (1989). In the latter technique mutations are introduced at every residue in the molecule, and the resultant mutant molecules are tested for biological (i.e. transglutaminase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., (1992); Smith et al., (1992); Wlodaver et al., (1992).

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970)). Using GAP e.g. with the following settings for DNA sequence comparison: GAP creation penalty of 5.0 and GAP extension penalty of 0.3, the coding region of the DNA sequence may exhibit a degree of identity preferably of at least 80%, more preferably at least 82%, more preferably at least 85%, especially at least 90%, with the coding region of the DNA sequence shown in SEQ ID No.1 or the DNA sequence obtainable from the plasmid in *E. coli*, DSM 10175.

The homology referred to in ii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970)). Using GAP e.g. with the following settings for polypeptide sequence comparison: GAP creation penalty of 3.0 and GAP extension penalty of 0.1, the polypeptide encoded by an analogous DNA sequence may exhibit a degree of identity preferably of at least 79%, more preferably at least 80%, even more preferably at least 82%, especially at least 90%, with the enzyme encoded by a DNA construct comprising the DNA sequence shown in SEQ ID No.1 or the DNA sequence obtainable from the plasmid in *E. coli*, DSM 10175.

In connection with property iii) above it is intended to indicate an transglutaminase encoded by a DNA sequence isolated from strain DSM 10175 and produced in a host organism transformed with said DNA sequence or produced by the strain DSM 10175. The immunological reactivity may be determined by the method described in the Materials and Methods section below.

In further aspects the invention relates to an expression vector harbouring a DNA construct of the invention, a cell comprising the DNA construct or expression vector and a method of producing an enzyme exhibiting transglutaminase activity which method comprises culturing said cell under conditions permitting the production of the enzyme, and recovering the enzyme from the culture.

In a still further aspect the invention relates to an enzyme exhibiting transglutaminase activity, which enzyme
a) is encoded by a DNA construct of the invention
b) produced by the method of the invention, and/or
c) is immunologically reactive with an antibody raised against a purified transglutaminase encoded by the DNA sequence shown in SEQ ID No.1 or the DNA sequence obtainable from the plasmid in *E. coli*, DSM 10175.

The transglutaminase mentioned in c) above may be encoded by the DNA sequence isolated from the strain *E. coli*, DSM 10175, and produced in a host organism transformed with said DNA sequence or produced by the strain *Streptomyces lydicus*, the strain *Streptomyces lydicus*, NRRL B-3446, provided by and publicly available from Agricultural Research Service Culture Collection, 1815 North University Street, Peoria, Ill. 61604, U.S.A.

The DNA sequence of the invention encoding an enzyme exhibiting transglutaminase activity may be isolated by a general method involving cloning, in suitable vectors, a DNA library from *Streptomyces lydicus*, transforming suitable bacterial or yeast host cells with said vectors, culturing the host cells under suitable conditions to express any enzyme of interest encoded by a clone in the DNA library, screening for positive clones by determining any transglutaminase activity of the enzyme produced by such clones, and isolating the enzyme encoding DNA from such clones.

The general method is further disclosed in WO 94/14953 the contents of which are hereby incorporated by reference. A more detailed description of the screening method is given in Example 15 below.

The DNA sequence of the DNA construct of the invention may be isolated by well-known methods. Thus, the DNA sequence may, for instance, be isolated by establishing a cDNA or genomic library from an organism expected to harbour the sequence, and screening for positive clones by conventional procedures. Examples of such procedures are hybridization to oligonucleotide probes synthesized on the basis of the full amino acid sequence shown in SEQ ID No. 2, or a subsequence thereof in accordance with standard techniques (cf. Sambrook et al., 1989), and/or selection for clones expressing a transglutaminase activity as defined above, and/or selection for clones producing a protein which is reactive with an antibody raised against the transglutaminase enzyme comprising the amino acid sequence shown in SEQ ID No. 2.

A preferred method of isolating a DNA construct of the invention from a cDNA or genomic library is by use of polymerase chain reaction (PCR) using degenerate oligonucleotide probes prepared on the basis of the amino acid sequence of the parent transglutaminase enzyme. For in stance, the PCR may be carried out using the techniques described in U.S. Pat. No. 4,683,202 or by R. K. Saiki et al. (1988).

Alternatively, the DNA sequence of the DNA construct of the invention may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA construct may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire recombinant DNA molecule, in accordance with standard techniques.

The DNA sequence coding for the transglutaminase enzyme may for instance be isolated by screening a DNA library of *Streptomyces lydicus,* and selecting for clones expressing the appropriate enzyme activity (i.e. transglutaminase activity) or from *E. coli,* DSM 10175, deposited under the Budapest Treaty on Aug. 23, 1995, at DSM (Deutsche Sammlung von Mikroorganismen und Zellkulturen GmbH, Mascheroder Weg 16, D-38124 Braunschweig, Germany). The appropriate DNA sequence may then be isolated from the clone e.g. as described in Example 1.

It is expected that a DNA sequence coding for a homologous enzyme, i.e. an analogous DNA sequence, is obtainable from other microorganisms. For instance, the DNA sequence may be derived by similarly screening a DNA library of another bacterium, preferably a gram-positive bacterium, more preferably a strain of a Streptomyces sp., in particular a strain of *S. platensis.*

Alternatively, the DNA coding for a transglutaminase of the invention may, in accordance with well-known procedures, conveniently be isolated from DNA from a suitable source, such as any of the above mentioned organisms, by use of synthetic oligonucleotide probes prepared on the basis of a DNA sequence disclosed herein. For instance, a suitable oligonucleotide probe may be prepared on the basis of the nucleotide sequence shown in SEQ ID No. 1 or any suitable subsequence thereof.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the transglutaminase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the transglutaminase, the promoter and the terminator, respectively, and to insert them into suitable vectors are well known to persons skilled in the art (cf., for instance, Sambrook et al., Molecular Cloning. A Laboratory Manual, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell, or a prokaryotic cell such as a bacterial cell. In particular, the eukaryotic cell may belong to a species of Aspergillus, Fusarium or Trichoderma, most preferably *Aspergillus oryzae, Aspergillus nidulans* or *Aspergillus niger.* Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces kluyveri* or *Saccharomyces uvarum,* a strain of Schizosaccaromyces sp., such as *Schizosaccharomyces pombe,* a strain of Hansenula sp., Pichia sp., Yarrowia sp. such as *Yarrowia lipolytica,* or Kluyveromyces sp. such as *Kluyveromyces lactis.* The host cell may also be a bacterial cell, preferably a strain of gram positive bacteria, more preferably Bacillus or Streptomyces, especially *Bacillus subtilis, Bacillus licheniformis, Bacillus lentus, Bacillus brevis, Bacillus stearothermophilus, Bacillus alkalophilus, Bacillus amyloliguefaciens, Bacillus coagulans, Bacillus circulans, Bacillus lautus, Bacillus megaterium, Bacillus thuringiensis,* or *Streptomyces lividans, S. lydicus* or *Streptomyces murinus;* or gram negative bacteria, preferably Escherichia, more preferably *E.coli.* The transformation of the bacteria may for instance be effected by protoplast transformation or by using competent cells in a manner known per se.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. (1989)).

The expression vector of the invention may also comprise a suitable transcription terminator and, in eukaryotes, polyadenylation sequences operably connected to the DNA sequence encoding the protein disulfide redox agent of the invention. Termination and polyadenylation sequences may suitably be derived from the same sources as the promoter.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed transglutaminase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like. The expressed transglutaminase may also be cell wall bound.

Composition of the Invention

Although the useful transglutaminase may be added as such it is preferred that it is formulated into a suitable composition. The transglutaminase to be used industrially may be in any form suited for the use in question, e.g. in the form of a dry powder or granulate, in particular a non-dusting granulate, a liquid, in particular a stabilized liquid, or a protected enzyme. Granulates may be produced, e.g. as disclosed in U.S. Pat. Nos. 4,106,991 and 4,661,452, and may optionally be coated by methods known in the art. Liquid enzyme preparations may, for instance, be stabilized by adding nutritionally acceptable stabilizers such as a sugar, a sugar alcohol or another polyol, lactic acid or another organic acid according to established methods. Protected enzymes may be prepared according to the method disclosed in EP 238,216. The enzyme preparation of the invention may also comprise a preservative.

Normally, for inclusion in flour, meat products, cheese and other milk products, fish products, cosmetics, various gelled food, it may be advantageous that the enzyme preparation is in the form of a dry product, e.g. a non-dusting granulate, whereas for inclusion together with a liquid it is advantageously in a liquid form.

The invention is further illustrated in the following non-limiting examples.

EXAMPLE 1
Identification of Microorganisms that Produce Transglutaminases

The detection limit of the $[1,4-^{14}C]$-putrescine incorporation assay was found to be $\frac{1}{20}$ of the detection limit of the hydroxamate assay. The assay used is a slightly modified version of the original procedure (Curtis, C. G. & Lorand, L. (1976)). The transglutaminase activity is measured as incorporation of $[1,4-^{14}C]$putrescine into α-casein.

A. Transglutaminase-producing Fungi

Transglutaminases have been identified in culture broths of several microorganisms of fungal origin using the assay desribed in detail below. It was not possible to detect these transglutaminase activities using the hydroxamate assay (Folk, J. E. & Cole, P. W. (1966)) as described in EP-A-0 481 504.

The fungi were inoculated into shake flasks by harvesting mycelium from PDA slants (39 g/l potato dextrose agar). The shake flasks contain either medium E (4 g/l meat extract, 4 g/l yeast extract, 40 g/l glucose, 8 g/l tryptone, 0.001 g/l $FeSO_4$ 7 $H_2O$, 2 tablets/l EBIOS, pH 7.0), medium D (50 g/l potato meal, 25 g/l barley meal, 0.025 g/l BAN 800 MG, 5 g/l Na-casein, 10 g/l soy meal, 4.5 g/l $Na_2HPO_4$, 0.05 ml/l pluronic), medium A (75 g/l potato meal, 0.075 g/l BAN 800 MG, 40 g/l soy meal, 9 g/l $Na_2HPO_4$, 1.5 g/l $KH_2PO_4$, 0.1 ml/l pluronic), medium F (4 g/l yeast extract, 15 g/l glucose, 1 g/l $K_2HPO_4$, 0.5 g/l $MgSO_4$, pH 7,0), medium B (30 g/l soy meal, 15 g/l malto dextrine, 5 g/l bacto peptone, 0.2 g/l pluronic), medium G (Glucose 40 g/l, Soytone 10 g/l, $CaCl_2$ 10 mg/l, $FeSO_4$ 10 mg/l, $MnSO_4.4H_2O$ 1 mg/l, $ZnSO_4.7H_2O$ 1 mg/l, $CuSO_4.5H_2O$ 2 mg/l, Softwood pulp (unbleached pine) 2.5 g/l (dry weight), pH adjusted to 5.0) or medium C ($KH_2PO_4$ 0.2 g/l; $MgSO_4$, 7 $H_2O$ 0.05 mg/l; $CaCl_2,2$ $H_2O$ 0.013 mg/l; $(NH_4)H_2PO_4$ 0.24 mg/l; 0.01 M Na-acetat (pH 4.5); mineral solution 7 ml/l; glucose 1 g/l; destilled water 863 ml/l; pH adjusted to 6.0; agar 15 g/l; thiamine (after autoclaving) 1 mg/l). The cultures were cultured at 26° C. for 3–30 days with shaking. The resulting culture broth were centrifuged 10 minutes at 2300 g to give cell free culture broths (transglutaminase preparations).

To 20 μl of sample is added 5 μl $[1,4-^{14}C]$putrescine (1.85 MBq/ml in 2% aqueous ethanol; specific activity 4.22 GBq/mmol) and 20 μl α-casein (2% in 50 mM Tris-HCl, 100 mM NaCl, 5 mM DTT, pH 7.5). Incubation takes place for 2 h at room temperature following which 30 μl of the assay mixture is spotted onto a small round Whatman 3MM filter. The filter is immediately put into a basket submerged in cold 10% trichloroacetic acid and washed for 20 min to remove excess radioactivity. After this first wash the filters are washed three times with cold 5% trichloroacetic acid, one time with cold ethanol:acetone (50:50, v:v) and one time with cold acetone. Each of these washes takes place for 5 min. In all washing steps the amount of washing liquid should be at least 5 ml/filter. The washed filters are counted directly in scintillation vials.

Units: An enzyme activity which incorporates 1 nmol $[1,4-^{14}C]$-putrescine per hour is defined as 1 U.

The tables below disclose species that produce transglutaminases in the specified growth medium upon cultivation. The enzyme activities are shown in terms of units of transglutaminase activity.

|  | Medium | Units/ml | Dep. No. |
|---|---|---|---|
| Transglutaminase positive basidiomycotina | | | |
| Class: Hymenomycetes | | | |
| Order: Agaricales | | | |
| Family: Agaricaceae | | | |
| Agaricus sp. | A | 0.15 | — |
| Chamaemyces fracidus | B | 0.20 | — |
| Family: Amanitaceae | | | |
| Amanita virosa | B | 0.14 | — |
| Family: Coprinaceae | | | |
| Coprinus cinereus | B | 0.14 | IFO 30116 |
| Coprinus sp. | C | 0.44 | — |
| Psathyrella condolleana | B | 0.19 | CBS 628.95 |
| Panaeolus papilionaceus | C | 0.15 | CBS 630.95 |
| Family: Strophariaceae | | | |
| Stropharia coerulea | B | 0.16 | — |
| Hypholoma fasciculare | B | 0.14 | — |
| Kuhneromyces variabilis | B | 0.14 | — |
| Pholiota jahnii | B | 0.21 | — |

-continued

| | Medium | Units/ml | Dep. No. |
|---|---|---|---|
| Family: Tricholomataceae | | | |
| Tricholoma flavovirens | B | 0.16 | — |
| Tricholoma myomyces | B | 0.23 | — |
| Lyophyllum sp. | D | 0.25 | — |
| Armillaria sp. | D | 0.62 | CBS 372.94 |
| Family: Polyporaceae | | | |
| Pleurotus dryinus | B | 0.22 | — |
| Pleurotus sp. | B | 2.36 | — |
| Family: Paxillaceae | | | |
| Hygrophoropsis aurantiaca | B | 0.17 | — |
| Family: Cortinariaceae | | | |
| Gymnopilus junonius | B | 0.20 | — |
| Order: Aphyllophorales | | | |
| Family: Coriolaceae | | | |
| Pycnoporus cinnabarinus | B | 0.14 | |
| Family: Fomitopsidaceae | | | |
| Antrodia serialis | D | 0.80 | |
| Trametes hirsuta | B | 0.21 | |
| Family: Stereaceae | | | |
| Amylostereum chailletii | D | 0.44 | CBS 373.94 |
| Family: Hymenochaetaceae | | | |
| Hymenochaete corticola | C | 1.31 | CBS 371.94 |
| Family: Lachnocladiaceae | | | |
| Scytinostroma portentosum | B | 0.14 | — |
| Order: Ceratobasidiales | | | |
| Family: Ceratobasidiaceae | | | |
| Rhizoctonia solani | D | 0.17 | — |
| Order: Auriculariales | | | |
| Family: Auriculariaceae | | | |
| Auricularia polytricha | A | 0.18 | — |
| Class: Gasteromycetes | | | |
| Order: Nidulariales | | | |
| Family: Nidulariaceae | | | |
| Nidula sp. | B | 0.14 | — |
| Transglutaminase positive ascomycetes | | | |
| Class: Loculoascomycetes | | | |
| Order: Dothideales | | | |
| Family: Pleosporaceae | | | |
| Alternaria alternata | A | 0.16 | CBS 448.94 |
| Cochliobolus sativus | B | 0.09 | — |
| Curvularia borreiae | D | 0.28 | CBS 859.73 |
| Family: Mycosphaerellaceae | | | |
| Cercospora beticola | A | 1.58 | ATCC 28056 |
| Cercospora carisis | A | 13.0 | IMI 167.425 |
| C. fusimaculans | A | 1.3 | IMI 167.426 |
| Cercospora hayi | A | 0.26 | IMI 160.414 |
| Cercospora sesami | A | 0.24 | IMI 318.913 |
| C. traversiana | A | 0.53 | IMI 318.080 |
| Cladosporium cladosporiodes | A | 0.22 | — |
| Cladosporiuin resinae | B | 0.14 | CBS 174.61 |
| C. oxysporum | A | 0.19 | — |
| C. sphaerospermum | A | 1.07 | CBS 444.94 |

-continued

| | Medium | Units/ml | Dep. No. |
|---|---|---|---|
| Family: Botryosphaeriaceae | | | |
| Botryosphaeria rhodina | A | 0.32 | — |
| Family: Sporormiaceae | | | |
| Sporormiella australis | E | 0.13 | — |
| Sporormiella minima | D | 0.20 | — |
| Preussia isomera | D | 0.22 | — |
| Family: Herpotrichiellaceae | | | |
| Carponia solliomaris | A | 0.11 | — |
| Family: Unknown family | | | |
| Coniothyrium cerealis | D | 0.13 | — |
| Class: Pyrenomycetes | | | |
| Order: Xylariales | | | |
| Family: Xylariaceae | | | |
| Xylaria sp | E | 0.28 | — |
| Ascotricha erinacea | A | 0.15 | — |
| Nodulisporium sp. | D | 1.20 | — |
| Family: Amphisphaeriaceae | | | |
| Savoryella lignicola | A | 6.24 | CBS 626.95 |
| Order: Diaporthales | | | |
| Family: Valsaceae | | | |
| Valsa pini | D | 0.73 | — |
| Order: Sordariales | | | |
| Family: Chaetomiaceae | | | |
| Chaetomium funicolum | B | 0.16 | ATCC 42779 |
| Family: Lasiosphaeriaceae | | | |
| Podospora tetraspora | D | 0.30 | — |
| Order: Halosphaeriales | | | |
| Family: Halosphaeriaceae | | | |
| Halosphaeriopsis mediosetigera | D | 0.34 | — |
| Lulworthia uniseptata | E | 0.36 | IFO 32137 |
| Lignincola sp. | D | 0.15 | — |
| Order: Hypocreales | | | |
| Family: Hypocreaceae | | | |
| Fusarium armeniacum | D | 0.19 | IBT 2173 |
| Fus. decemcellulare | B | 0.10 | CBS 315.73 |
| Fusarium dimerum | B | 0.25 | IBT 1796 |
| Fusarium merismoides | D | 0.16 | ATCC 16561 |
| Fusarium redolens | B | 0.16 | IBT 2059 |
| Fusarium flocciferum | D | 0.15 | — |
| Myrothecium roridum | B | 0.13 | ATCC 20605 |
| Trichoderma harzianum | A | 0.25 | CBS 223.93 |
| Class: Discomycetes | | | |
| Order: Leotiales | | | |
| Family: Leotiaceae | | | |
| Dimorphosporum disporatrichum | A | 0.42 | ATCC 24562 |
| Class: Plectomycetes | | | |
| Order: Eurotiales | | | |
| Family: Trichocomataceae | | | |
| Byssochlamys fulva | A | 0.24 | AHU 9252 |
| Talaromyces helicus | B | 0.23 | ATCC 10451 |
| Neosartorya quadricineta | D | 0.22 | IBT 11057 |
| Warcupiella spinulosa | D | 0.41 | NKBC 1495 |
| Aspergillus foetidus | A | 0.23 | CBS 565.65 |
| Aspergillus giganteus | C | 0.19 | CBS 526.65 |

-continued

| | Medium | Units/ml | Dep. No. |
|---|---|---|---|
| *Asp. heteromorphus* | C | 0.12 | CBS 117.55 |
| *Aspergillus puniceus* | F | 0.12 | IAM 13893 |
| *Aspergillus tamarii* | A | 0.16 | IBT 3824 |
| Order: Ascomycetes of unknown order | | | |
| *Beauveria cylindrospora* | A | 0.24 | CBS 719.70 |
| *Beauveria calendonica* | A | 0.25 | CBS 485.88 |
| *Hortea werneckii* | A | 0.95 | CBS 446.94 |
| *Humicola alopallonella* | C | 0.76 | — |
| *Monodictys pelagica* | A | 2.31 | CBS 625.95 |
| *Dendryphiella salina* | D | 0.96 | CBS 447.94 |
| Transglutaminase positive zygomycetes | | | |
| Order: Mucorales | | | |
| *Mucor aligarensis* | D | 0.31 | ATCC 28928 |
| *Mucor luteus* | B | 0.34 | — |
| *Cunninghamella elegans* | B | 0.23 | AHU 9445 |

B. Transglutaminase-producing Bacteria

Bacteria grown on Tryptone-yeast agar-plates were used for inoculation of shake flasks. The shake flasks contained 100 ml the media listed below. Cultures were incubated at 30° C. for 1–12 days while shaking at 250 rpm. Samples (5 ml) were taken from the broth and analyzed for Tgase activity either in the crude broth, in cell-free supernatant (after centrifugation for 15 min at 2300×g) or in the cell-pellet which was resuspended in an equal amount of sterile medium.

The table below shows examples of bacterial species that produce TGase upon cultivation in the listed media. Tgase activity is given in units/ml.

| Genus/species | medium | units/ml | Dep. No. |
|---|---|---|---|
| *Streptomyces lydicus* | H | 1.3 | DSM 40555 |
| | | | NRRL B-3446 |
| *Streptomyces nigrescens* | A | 0.3 | ATCC 23941 |
| *Streptomyces sioyaensis* | H | 3.3 | ATCC 13989 |
| *Streptomyces platensis* | A | 1.4 | DSM 40041 |
| *Rothia dentocariosa* | J | 0.9 | — |
| *Bacillus badius* | K | 0.8 | DSM 23 |
| *Bacillus mycoides* | L | 0.4 | GJB 371 |
| *Bacillus firmus* | J | 0.6 | ATCC 17060 |
| *Bacillus firmus* | J | 0.03 | DSM 12 |
| *Bacillus aneurinolyticus* | N | 0.8 | ATCC 12856 |
| *Bacillus megaterium* | J | 0.02 | ATCC 13632 |
| *Bacillus megaterium* | J | 0.02 | ATCC 15450 |
| *Bacillus megaterium* | J | 0.03 | AJ 3355 |
| | | | Ferm-P 1201 |
| Bacillus sp. | J | 0.1 | ATCC 21537 |
| B. amyloliquefaciens | P | 0.06 | ATCC 23843 |
| Kitasatao purpurea | P | 0.3 | DSM 43362 |
| Bacteridium sp. (1) | A | 0.3 | DSM 10093 |
| Bacteridium sp. (1) | Q | 0.5 | CBS 495.74 |
| Pseudomonas putida | A | 0.84 | DSM 1693 |
| Pseudomonas putida | D | 1.4 | NCIMB 9869 |
| Pseudomonas amyloderamosa | N | 0.08 | ATCC 21262 |
| Hafnia alvei | K | 0.3 | DSM 30163 |
| Hydrogenophaqa palleroni | Q | 0.6 | DSM 63 |
| (Basonym: *Pseudomonas palleroni*) | | | |
| Zymomonas mobilis | N | 0.36 | DSM 424 |
| Moo5A10 (1) | L | 0.44 | DSM 10094 |

Note (1):
These strains are most probable Bacillus strains.

The used media were:

| Medium | Compound | Amount | pH |
|---|---|---|---|
| N | Tryptone | 20 g | 7.0 |
| | soluble starch | 20 g | |
| | $KH_2PO_4$ | 1 g | |
| | $MgSO_4$ | 1 g | |
| | Yeast extract | 2 g | |
| | Pluronic 100% | 0.5 g | |
| | Aqua dest | 1000 ml | |
| J | Trypticase | 40 g | 7.3 |
| | yeast extract | 10 g | |
| | $FeCl_2 \times 4H_2O$, 1% sol. | 1.2 ml | |
| | $MnCl_2 \times 4H_2O$, 1% sol. | 0.2 ml | |
| | $MgSO_4 \times 7H_2O$, 1% sol. | 3 ml | |
| | Aqua dest. | 1000 ml | |
| K | Casitone | 3 g | 6.5 |
| | $CaCl_2 \times 2 H_2O$ | 0.5 g | |
| | $MgSO_4 \times 7 H_2O$ | 2 g | |
| | Cyanocobalamine | 2 g | |
| | Trace elements (1) | 1 ml | |
| | Aqua dest | 1000 ml | |
| Q | Casitone | 1 g | 6.5 |
| | Yeast extract | 0.5 g | |
| | $CaCl_2 \times 2 H_2O$ | 0.5 g | |
| | $MgSO_4 \times 7 H_2O$ | 0.5 g | |
| | Glucose | 2 g | |
| | Aqua dest | 1000 ml | |
| L | Soluble starch | 15 g | 7.0 |
| | NaCl | 5 g | |
| | Corn steep liquid | 10 g | |
| | Crushed soy bean | 10 g | |
| | $CaCO_3$ | 2 g | |
| | Pluronic 100% sol. | 0.1 ml | |
| | Tap water | 1000 ml | |
| H | Glucose | 10 g | 7.0 |
| | Soluble starch | 30 g | |
| | Yeast extract | 7 g | |
| | Polypeptone | 7 g | |
| | NaCl | 3 g | |
| | $CaCO_3$ | 5 g | |
| | Tap water | 1000 ml | |
| P | Peptone | 6 g | 7.3 |
| | Pepticase | 4 g | |
| | Yeast extract | 3 g | |
| | Beef extract | 1.5 g | |
| | Dextrose | 1 g | |
| | Aqua demineralised | 1000 ml | |

Trace element solution for Medium K (mg/l Milli Q water): $MnCl_2 \times 4 H_2O$:100, $CoCl \times 6 H_2O$:36.34, $CuSO_4 \times 5 H_2O$:15.64, $Na_2MoO_4 \times 2 H_2O$:10, $ZnCl_2$:20, LiCl:5, $SnCl_2 \times 2 H_2O$:5, $H_3BO_3$:310, KBr: 20, KI: 20, $Na_2$-EDTA:8.

EXAMPLE 2

Media-dependent Expression of Transglutaminases

The amount of transglutaminase activity found in culture broths of the microorganisms was found to depend on the growth media used for cultivation. This is believed to be valid for all microorganisms, i.e. fungi or bacteria.

A. Fungi

The table below shows the transglutaminase activity found in the culture broth of the fungi *Hymenochaete corticola* and *Cercospora carisis*, respectively, cultivated on three different media (see example 1 for the compositions of the used media).

| Strain | Medium | Activity (U/ml) |
|---|---|---|
| Hymenochaete corticola | C | 1.31 |
| Hymenochaete corticola | B | 0 |
| Hymenochaete corticola | G | 0 |
| Cercospora carisis | C | 0.3 |
| Cercospora carisis | B | 0.4 |
| Cercospora carisis | A | 13 |

B. Bacteria

Also for bacteria the amount of TGase activity found in the culture broths of the bacteria was found to depend on the growth media used for cultivation.

Selected strains were grown in the different media (see above example 1) to investigate the effect of the medium on the expression of TGase activity. In the following table an example is given for *Pseudomonas putida* and *Hydrogenophaga palleroni* TGase. The other strains investigated were *Streptomyces lydicus*, *Pseudomonas putida* (DSM 1693), *Rothia dentocariosa*, *Bacillus firmus*, *Bacillus badius*, *Bacillus amyloliquefaciens*, *Bacillus aneurinolyticus*, *Bacillus megaterium* (3 strains, see example 1), *Bacillus mycoides*, *Zymomonas mobilis*, *Hafnia alvei*, *Kitasatao purpurea*, Bacteridium sp., strain Moo5A10.

| Medium | Activity (U/ml) Ps. putida (NCIMB 9869) | Activity (U/ml) Hy. palleroni |
|---|---|---|
| N | 0 | 0 |
| J | 0.08 | 0 |
| A | 1.4 | 0 |
| D | 1.4 | 0 |
| Q | 1.8 | 0.6 |
| L | 0.12 | 0.18 |
| H | 0.4 | 0 |
| P | 0.2 | 0.07 |

EXAMPLE 3

A. Temperature Dependency of Fungal Transglutaminases

The temperature dependency of the transglutaminase present in the transglutaminase preparation of *Cladosporium sphaeospermum*, *Cercospora carisis*, *Savoryella lignicola* and *Lulworthia unisepta* (see example 1 for deposition numbers) was investigated using a modification of the putrescine assay described in example 1.

For determination of the temperature dependency incubation took place for 1 hour at either room temperature, 40° C., 55° C., 60° C., 70° C., 80° C. or 90° C.

The table below shows the temperature dependencies of the fungal transglutaminases. The enzyme activities are given in relative activities.

| Strain | Relative activities at temperature | | | | | | |
|---|---|---|---|---|---|---|---|
| | RT | 40° C. | 55° C. | 60° C. | 70° C. | 80° C. | 90° C. |
| Cercospora carisis | 33 | 100 | 54 | 21 | 20 | 27 | 8 |
| Cladosporium sphaeospermum | 19 | 41 | 58 | 68 | 84 | 100 | 41 |
| Savoryella lignicola | 17 | 75 | 100 | 88 | 12 | 10 | 6 |
| Lulworthia uniseptata | 7 | 15 | 24 | 27 | 41 | 69 | 100 |
| Hymenochaete corticola | 8 | 17 | 29 | 40 | 46 | 52 | 100 |
| Monodictys pelagica | 23 | 77 | 100 | 47 | 36 | 73 | 74 |

B. Temperature Dependency of Bacterial Transglutaminases

In this experiment temperature-dependencies of Tgases were examined in the following strains: *Pseudomonas putida* (NCIMB 9869), Bacteridium sp. (DSM 10093), strain Moo5A10, *Bacillus firmus*, *Bacillus badius* and *Rothia dentocanriosa*.

TGase containing samples from these strains were assayed at 20, 30, 40 and 55° C. (2 h of incubation). Samples were either cell-free culture fluid (*Pseudomonas putida*, Bacteridium sp., strain Moo5A10), centrifuged cells resuspended in sterile medium (*Bacillus firmus*, *Bacillus badius*) or crude culture broth (*Rothia dentocariosa*).

| Strain | 20° C. | 30° C. | 40° C. | 55° C. |
|---|---|---|---|---|
| Pseudoinonas putida | 31 | 100 | 55 | 55 |
| Bacteridium sp. | 53 | 77 | 100 | 78 |
| Moo5A10 | 83 | 85 | 100 | 96 |
| Bacillus firmus | 70 | 100 | 68 | 41 |
| Bacillus badius | 46 | 48 | 100 | 33 |
| Rot. dentocariosa | 78 | 67 | 70 | 100 |

EXAMPLE 4

A. pH Dependency of Fungal Transglutaminases

The pH dependency of the transglutaminase present in the transglutaminase preparation of *Cladosporium sphaeospermum*, *Cercospora carisis*, *Savoryella lignicola* and *Lulworthia unisepta* was investigated using a modification of the putrescine assay described in example 1.

A 4% α-casein solution was made in 50 mM Tris-HCl, 100 mM NaCl, pH 7.5 and diluted 1:1 in a modified 200 mM Britton-Robinson buffer (0.1 M $CH_3COOH$, 0.2 M $H_3BO_3$) at the pH values mentioned below. Before assaying, $CaCl_2$ and cysteine were added to a final concentration of 5 mM and 1 mM, respectively.

For pH dependency determination incubation takes place at room temperature for 1 hour at pH 7.0, 7.5, 8.0, 8.5 or 9.0.

The table below shows the pH dependencies of the fungal transglutaminases. The enzyme activities are given in relative activities.

|  | Relative activities at pH | | | | |
| --- | --- | --- | --- | --- | --- |
| Strain | 7.0 | 7.5 | 8.0 | 8.5 | 9.0 |
| Cercospora carisis | 77 | 78 | 78 | 100 | 66 |
| Cladosporium sphaeospermum | 53 | 56 | 67 | n.d | 100 |
| Savoryella lignicola | 63 | 69 | 75 | n.d | 100 |
| Lulworthia uniseptata | 15 | 21 | 39 | n.d. | 100 |
| Hymenochaete corticola | 11 | 12 | 24 | n.d. | 100 |
| Monodictys pelagica | 15 | 32 | 43 | n.d. | 100 | n.d.: not determined.

B. pH Dependency of Bacterial Transglutaminases

TGase activities from selected strains were investigated using modified Britton-Robinson buffer adjusted to pH 6.5, 7, 7.5, 8, 8.5 and 9. A 4% α-casein solution was made in 50 mM Tris/HCl, 100 mM NaCl, pH 7.5 and diluted 1:1 in 200 mM Britton-Robinson buffer (0.1 M CH3COOH, 0.2 M H3BO3) at the pH values mentioned above.

The TGase activity was measured at 20° C. in a standard assay with 2 hours incubation and 2 mM EDTA. The strains investigated were Bacteridium sp., Moo5A10, *Bacillus firmus, Bacillus mycoides, Bacillus badius, Bacillus aneurinolyticus, Rothia dentocariosa*.

Results

|  | Relative activity (%) | | | | | |
| --- | --- | --- | --- | --- | --- | --- |
| Strain | pH 6.5 | pH 7 | pH 7.5 | pH 8 | pH 8.5 | pH 9 |
| Bacteridium sp. | 72 | 85 | 76 | 86 | 88 | 100 |
| Moo5A10 | 37 | 38 | 44 | 59 | 76 | 100 |
| Bacillus firmus | 15 | 20 | 28 | 40 | 70 | 100 |
| Bacillus mycoides | 63 | 78 | 66 | 84 | 100 | 67 |
| Bacillus badius | 43 | 46 | 49 | 65 | 76 | 100 |
| B. aneurinolyticus | 47 | 47 | 57 | 39 | 100 | 72 |
| Rot. dentocariosa | 100 | 63 | 62 | 64 | 61 | 38 |

EXAMPLE 5

A. $Ca^{2+}$-dependency of Fungal Transglutaminases

The $Ca^{2+}$-dependency of the transglutaminase present in the transglutaminase preparation of *Cercospora carisis* and *Savoryella lignicola* was investigated using the modified putrescine assay described in example 1.

The transglutaminase preparations were concentrated approximately 10 times using a Macrosep™ concentrators from Filtron. Following the samples were diluted 10 times in 50 mM Tris-HCl, 100 mM NaCl, 1 mM cysteine, pH 7.5 ($-Ca^{2+}$) or in 50 mM Tris-HCl, 100 mM NaCl, 1 mM cysteine+5 mM $CaCl_2$, pH 7.5 ($+Ca^{2+}$).

For determination of the $Ca^{2+}$-dependency the incubation took place at 40° C. for 1 hour. The α-casein was dissolved in either 50 mM Tris-HCl, 100 mM NaCl, 1 mM cysteine, pH 7.5 or in 50 mM Tris-HCl, 100 mM NaCl, 1 mM cysteine+5 mM $CaCl_2$, pH 7.5

The results are shown in the table below:

|  | Relative activities | |
| --- | --- | --- |
| Strain | $-Ca^{2+}$ | $+Ca^{2+}$ |
| Savoryella lignicola | 70 | 100 |
| Cercospcra carisis | 99 | 100 |

B. $Ca^{2+}$dependency of Bacterial Transglutaminases

The effect of $Ca^{2+}$-ions on Tgase activity was investigated in selected $Ca^{2+}$-free samples derived after centricon treatment. The samples were applied to a 10 kD Centricon concentrator, centrifuged (no activity in the filtrate), the enzymes in the retentate were resuspended in an equal amount of $Ca^{2+}$-free Tris-buffer (0.1 M, pH 7.5) and centrifuged again to resolve them from the filtre. All samples were concentrated and diluted for a second time in order to ensure $Ca^{2+}$-free conditions.

Samples from the second centricon treatment were incubated both in the presence (2 mM CaCl2) and in the absence of $Ca^{2+}$(5 mM EDTA) to determine $Ca^{2+}$-effects. TGase activity was measured before the centricon treatment (set to 100%) and after first and second centricon treatment. Only selected strains were investigated: Bacteridium, Moo5A10, *Bacillus firmus* and *Bacillus badius*.

The results were:

|  | Relative TGase activity | | | | |
| --- | --- | --- | --- | --- | --- |
|  | bef. | after 1st centricon | | after 2nd centricon | |
| species | centr. | $-Ca++$ | $+Ca++$ | $-Ca++$ | $+Ca++$ |
| Bacteridium sp. | 100 | 99 | n.d. | 76 | 129 |
| Moo5A10 | 100 | 96 | n.d. | 104 | 112 |
| Bacillus firmus | 100 | 78 | n.d. | 60 | 79 |
| Bacillus badius | 100 | 5 | 52 | n.d. | n.d. | n.d. = not determined

In this experiment TGases investigated from Bacteridium, Moo5A10 and *Bacillus firmus* are $Ca^{2+}$-independent: Activity after filtration in an EDTA containing assay was about as high as before centrifugation in the untreated sample (80–99%). After 2nd centricon the activity is slightly stimulated by the addition of $Ca^{2+}$ for Moo5A10 and Bacteridium. For Bacteridium still about 80% and for Moo5A10 about 93% of activity were measured without $Ca^{2+}$. Therefore these activities are defined as $Ca^{2+}$-independent.

*Bacillus badius* TGase was $Ca^{2+}$-dependent: after first centricon no activity (5%) was measured without added $Ca^{2+}$. The activity could be restored after adding 2 mM $Ca^{2+}$ to about 50%.

EXAMPLE 6

Polymerization of Casein with Transglutaminases

The cell free culture broths of several selected transglutaminase producing microorganisms were investigated for their ability to polymerize casein in solution. In addition, two purified microbial transglutaminases were also investigated.

In general, 100 μl sample were mixed with 20 μl 0.1 M glutathion in 0.2 M Tris-HCl, pH 7.9 and 100 μl 1.5% α-casein in 0.2 M Tris-HCl, pH 7.9 and incubated for various times at 37° C. The reaction was stopped by mixing 20 μl incubation mixture with 20 μl sample buffer for SDS-PAGE analysis followed by heating at 95° C. for 10 min. The polymerization was visualised by SDS-PAGE.

The fermentation broths investigated were from *Streptomyces lydicus, Cercospora carisis, Cladospozium sphaeospermum* and *Savoryella lignicola* while the purified samples were from *Streptomyces lydicus* and *Streptomyces platensis*.

The experiment was also carried out with fermentation broth from *Lulworthia uniseptata* with the only difference being that the incubation took place at 70° C. and at 90° C. In addition, the experiment was carried out with fermentation broth from *Cladosporium sphaeospermum* with incubation at 80° C.

In all cases the incubation resulted in the rapid formation of casein polymers of very high molecular mass formed concomitant with the reduction of α-casein monomers.

EXAMPLE 7
Purification of the Transglutaminase from *Streptomyces lydicus*, NRRL B-3446 (Former *Streptomyces libani*)

*Streptomyces lydicus*, NRRL B-3446 (former *Streptomyces libani*), was inoculated into 1 l Zym medium (20 g/l yeast extract, 12 g/l glucose, 10 g/l bactopeptone, 0.01% pluronic, pH 6.5) and cultured with shaking at 30° C. for 24 h. The resulting seed culture solution was added to 16 l of Zym medium which was then cultured with shaking at 30° C. for 4 days. The resulting culture broth was filtered to give 11.8 l of culture filtrate. The transglutaminase activity in the culture filtrate was 3 U/ml.

The culture filtrate was concentrated six times using a Filtron Minisette membrane with 3 kDa cut off. From a 500 ml portion of the concentrate the transglutaminase was precipitated by adding ammonium sulfate to 65% saturation at ambient temperature. The precipitate was dissolved in 10 mM sodium acetate pH 6.0. After extensive dialysis against 10 mM sodium acetate pH 6.0 the sample was passed through a SP-Sepharose column equilibrated with 10 mM sodium acetate pH 6.0. The transglutaminase was eluted using a linear gradient from 0 to 0.5 M sodium chloride. Fractions with high specific activity were collected and the pool was concentrated in an Amicon cell equipped with a Diaflo membrane with 10 kDa cut off. A buffer change to 20 mM sodium phosphate pH 6.5 was made in the Amicon cell. The last impurities in the preparation was removed by passing it through a Blue-Sepharose column equilibrated with 20 mM sodium phosphate pH 6.5. The transglutaminase was eluted using a linear gradient from 0 to 1.0 M sodium chloride. The enzyme was pure as judged by SDS-PAGE and N-terminal sequencing. The specific activity of the pure transglutaminase was 90 times that of the culture filtrate.

EXAMPLE 8
Purification of the $Ca^{2+}$-independent Transglutaminase from *Streptomyces platensis*

*Streptomyces platensis* was inoculated into 500 ml H medium (7 g/l yeast extract, 10 g/l glucose, 7 g/l polypeptone, 30 g/l soluble starch, 3 g/l NaCl, 5 g/l $CaCO_3$, pH 7.0) and cultured with shaking at 30° C. for 24 h. The resulting seed culture solution was added to 8 l of H medium which was then cultured with shaking at 30° C. for 2 days. The resulting culture broth was filtered to give 5.0 l of culture filtrate. The transglutaminase activity in the culture filtrate was 2.4 U/ml.

The culture filtrate was concentrated to 300 ml using a Filtron Minisette membrane with 3 kDa cut off. After extensive dialysis against 10 mM sodium acetate, pH 5.5 the sample was passed through an S-Sepharose column equilibrated with 10 mM sodium acetate, pH 5.5. The transglutaminase was eluted using a linear gradient from 0 to 0.25 M sodium chloride. Fractions with high specific activity were collected and the pool was dialysed against 10 mM Tris-HCl, pH 9.0. The pool was applied in 5 ml aliqouts to a 1 ml Mono-Q Sepharose column equlibrated with 10 mM Tris-HCl, pH 9.0. The transglutaminase was eluted using a linear gradient from 0 to 0.25 M sodium chloride. The transglutaminase containing fractions were pooled and concentrated in an Amicon cell equipped with a Diaflo membrane with a 10 kDa cut off. A buffer change to 100 mM sodium phosphate, pH 6.5 was made in the Amicon cell. The last impurities in the preparation was removed by gelfiltration using a Superdex 75 column equlibrated in 100 mM sodium phosphate, pH 6.5. The enzyme was pure as judged by SDS-PAGE and N-terminal sequencing. The specific activity relative to the the culture filtrate was 800 times that of the culture broth.

The temperature optimum was found to be 45° C. and the pH optimum was found to be above pH 9.

EXAMPLE 9
Inhibition of the $Ca^{2+}$-independent Transglutaminase from *Streptomyces platensis*

As transglutaminases in general are considered to be dependent on the presence of a free Cys-residue the transglutaminase from *Streptomyces platensis* was incubated in the presence and absence of nine fold molar excess of inhibitor (50 μM) to cysteine. Four cysteine reactive compounds were used mono-iodoacetic acid, $ZnCl_2$, $HgCl_2$, and $FeCl_3$. Samples were incubated in the putrescine assay with and without inhibitor for 2 h at room temperature before the activity was measured. The incubations were carried out in duplicate.

In samples incubated with mono-iodoacetic acid, $ZnCl_2$, or $HgCl_2$ no residual activity was found. In the samples with $FeCl_3$ less than one percent residual activity was found. This is different from the results obtained by Ando et al. (Agric. Biol. Chem. 53(10), 2313–2317, 1989) with the transglutaminase from *S. mobaraense*. These authors find 76%, 89% and 11% residual activity after preincubation of the transglutaminase for 30 min at 25° C. with 1 mM mono-iodoacetic acid, 1 mM $FeCl_3$ and 1 mM $ZnCl_2$, respectively. Thus, the inhibition profiles of the two transglutaminases are clearly different.

EXAMPLE 10
Structural Characterization of the Transglutaminase from *Streptomyces lydicus*

Structural characterization of the transglutaminase was carried out on a small amount of highly purified enzyme (1.5 ml; $A_{280}$=0.3). One fifth was used for direct N-terminal amino acid sequencing. The remaining material was lyophilyzed and redissolved in 350 μl 6 M guanidinium chloride, 0.3 M Tris-HCl, pH 8.3 and denatured overnight at 37° C. The solution was added 10 μl 0.1 M DTT and incubated for 4 h at room temperature before addition of 20 μl 0.5 M freshly prepared $ICH_2COOH$. The reduced and S-carboxymethylated sample was desalted using a NAP5 column (Pharmacia) equilibrated and eluted with 20 mM $NH_4HCO_3$.

Following vacuum concentration the S-carboxymethylated transglutaminase was degraded for 16 h at 37° C. with 10 μg of lysine-specific protease (Achromobacter protease I). The resulting peptides were fractionated using reversed phase HPLC on a Vydac C18 column eluted with a linear gradient of 80% 2-propanol in 0.1% TFA. Selected peptide fractions were subjected to repurification using reversed phase HPLC on another Vydac C18 column eluted with linear gradients of 80% acetonitrile in 0.1% TFA.

N-terminal amino acid sequencing of the intact transglutaminase as well as sequencing of the purified peptides were done in an Applied Biosystems 473A protein sequencer operated according to the manufacturers instructions.

The sequences obtained are the following:

N-terminal sequence:
Ala-Ala-Asp-Glu-Arg-Val-Thr-Pro-Pro-Ala-Glu-Pro-Leu-Asn -Arg-Met-Pro-Asp-Ala-Tyr-Arg-Ala-Tyr-Gly-Gly-Arg-Ala-Thr -Thr-Val-Val-Asn-Asn-Tyr-Ile-Arg-Lys-Trp-Gln-(positions 1–39 of SEQ ID NO:2)

Peptide 1:
Trp-Gln-Gln-Val-Tyr-Ala-His-Arg-Asp-Gly-Ile-Gln-Gln-Gln -Met-Thr-Glu-Glu-Gln-Arg-Glu-(positions 38–58 of SEQ ID NO:2)

Peptide 2:
Leu-Ala-Phe-Ala-Phe-Phe-Asp-Glu-Asn-Lys (positions 80–89 of SEQ ID NO:2)

Peptide 3:
Ser-Asp-Leu-Glu-Asn-Ser-Arg-Pro-Arg-Pro-Asn-Glu-Thr-Gln -Ala-Glu-Phe-Glu-Gly-Arg-Ile-Val-Lys (positions 92–114 of SEQ ID NO:2)

Peptide 4:
Gly-Phe-Lys (positions 122–124 of SEQ ID NO:2)

Peptide 5:
Ala-Leu-Asp-Ser-Ala-His-Asp-Glu-Gly-Thr-Tyr-Ile-Asp-Asn -Leu-Lys (positions 136–151 of SEQ ID NO:2)

Peptide 6:
Thr-Glu-Leu-Ala-Asn-Lys (positions 152–157 of SEQ ID NO:2)

Peptide 7:
Asn-Asp-Ala-Leu-Arg-Tyr-Glu-Asp-Gly-Arg-Ser-Asn-Phe-Tyr -Ser-Ala-Leu-Arg-Asn-Thr-Pro-Ser-Phe-Lys (positions 158–181 of SEQ ID NO:2)

Peptide 8:
Glu-Arg-Asp-Gly-Gly-Asn-Tyr-Asp-Pro-Ser-Lys (positions 182–192 of SEQ ID NO:2) Peptide 9:
Ala-Val-Val-Tyr-Ser-Lys (positions 195–200 of SEQ ID NO:2)

Peptide 10:
His-Phe-Trp-Ser-Gly-Gln-Asp-Gln-Arg-Gly-Ser-Ser-Asp-Lys (positions 201–214 of SEQ ID NO:2)

Peptide 11:
Tyr-Gly-Asp-Pro-Asp-Ala-Phe-Arg-Pro-Asp-Gln-Gly-Thr-Gly -Leu-Val-Asp-Met-Ser-Lys (positions 217–236 of SEQ ID NO:2)

Peptide 12:
Asp-Arg-Asn-Ile-Pro-Arg-Ser-Pro-Ala-Gln-Pro-Gly-Glu-Ser -Trp-Val-Asn-Phe-Asp-Tyr-Gly-Trp-Phe-Gly-Ala-Gln-(positions 237–262 of SEQ ID NO:2)

Peptide 13:
Thr-Ile-Trp-Thr-His-Ala-Asn-His-Tyr-His-Ala-Pro-Asn-Gly -Gly-Leu-Gly-Pro-Met-Asn-Val-Tyr-Glu-Ser-Lys (positions 270–294 of SEQ ID NO:2)

Peptide 14:
Phe-Arg-Asn-Trp-Ser-Ala-Gly-Tyr-Ala-Asp-Phe-Asp-Arg-Gly -Thr-Tyr-Val-Ile-Thr-Phe-Ile-Pro-Lys (positions 295–317 of SEQ ID NO:2)

Peptide 15:
Ser-Trp-Asn-Thr-Ala-Pro-Ala-Glu-Val-Lys (positions 318–327 of SEQ ID NO:2)

Peptide 16 (C-terminal peptide):
Gln-Gly-Trp-Ser

Below are shown these sequences aligned to the sequence of a transglutaminase from Streptoverticillium (Kanaji et al., 1994; Washizu et al., 1994; EP-A-0481 504). Although the two enzymes are homologous they are clearly different as 22% (62 out of 279) of the residues sequenced from the *Streptomyces lydicus* transglutaminase differ from the corresponding residue in the Streptoverticillium transglutaminase. It should be stressed that many of the substitutions found are non-conservative—e.g. Asp1Ala, Pro19Ala, Pro22Ala, Ser23Tyr, Tyr24Gly, Glu28Thr, Thr29Val, Arg48Ile, Lys49Gln, Ser84Phe, Lys95Glu, Ser101Pro, Gly102Asn, Arg105Gln, Gln124Lys, Lys152Thr, Gly157Lys, Asn163Tyr, Pro169Asn, His188Tyr, Arg208Gln, Ser209Arg, Ala226Asp, Pro227Gln, Ala287Pro, His289Asn, Glu300Ala, Asp324Ala, Lys325Glu and Pro331Ser. The first mentioned residue is the one found in the transglutaminase from Streptoverticillium and the second residue is the one found in the transglutaminase from *Streptomyces lydicus*:

Alignment of the Peptide Sequences Obtained from *Streptomyces lydicus* Transglutaminase to the Amino Acid Sequence of Streptoverticillium Transglutaminase Upper sequence: *Streptomyces lydicus* transglutaminase
Lower sequence: streptoverticillium transglutaminase
Divergence: 62 out of 279 residues sequenced (22%)
Differences are marked with an asterisk (*)

```
           ** *         *    *   *** *              *   **
           AADERVTPPA EPLNRMPDAY RAYGGRATTV VNNYIRKWQQ VYAHRDGIQQ
         1 DSDDRVTPPA EPLDRMPDPY RPSYGRAETV VNNYIRKWQQ VYSHRDGRKQ

*   **    ** * *
           QMTEEQRE                        L AFAFFDENK  SDLENSRPR
        51 QMTEEQREWL SYGCVGVTWV NSGQYPTNRL AFASFDEDRF KNELKNGRPR

** *         **          *              **    ** *
           PNETQAEFEG RIVK       GFK            ALDSA HDEGTYIDNL
       101 SGETRAEFEG RVAKESFDEE KGFQRAREVA SVMNRALENA HDESAYLDNL

*         *  * *                    *   *   *   *
           KTELANKNDA LRYEDGRSNF YSALRNTPSF KERDGGNYDP SK  AVVYSK
       151 KKELANGNDA LRNEDARSPF YSALRNTPSF KERNGGNHDP SRMKAVIYSK

*** *                 **         *       ** *
           HFWSGQDQRG SSDK   YGDP DAFRPDQGTG LVDMSKDRNI PRSPAQPGES
```

```
                            -continued
201 HFWSGQDRSS SADKRKYGDP DAFRPAPGTG LVDMSRDRNI PRSPTSPGEG

*                       *  *        *  *  *             *
    WVNFDYGWFG AQ         T IWTHANHYHA PNGGLGPMNV YESKFRNWSA
251 FVNFDYGWFG AQTEADADKT VWTHGNHYHA PNGSLGAMHV YESKFRNWSE

*  *                         * *          *
    GYADFDRGTY VITFIPKSWN TAPAEVKQGW S
301 GYSDFDRGAY VITFIPKSWN TAPDKVKQGW P                          331
```

EXAMPLE 11
Structural Characterization of the $Ca^{2+}$-independent Transglutaminase from *Streptomyces platensis*

Structural characterization of the transglutaminase was carried out on an aliqout of highly purified enzyme (4 ml; $A_{280}$=0.74). The material was lyophilyzed and redissolved in 350 µl 6 M guanidinium chloride, 0.3 M Tris-HCl, pH 8.3 and denatured overnight at 37° C. The solution was added 5 µl 0.1 M DTT and incubated for 4 h at room temperature before addition of 25 µl 0.5 M freshly prepared $ICH_2COOH$. The reduced and S-carboxymethylated sample was desalted using a NAP5 column (Pharmacia) equilibrated and eluted with 20 mM $NH_4HCO_3$. The sample was lyophilized and redissolved in 500 µl 20 mM $NH_4HCO_3$. of the S-carboxymethylated transglutaminase 200 µl was added 20 µg of lysine-specific protease (Achromobacter protease I) and degraded for 16 h at 37° C. while another 200 µl was added 2 µg of the Asp-N protease from *Pseudomonas fragi* and degraded for 16 h at 37° C. The resulting peptides were fractionated using reversed phase HPLC on a Vydac C18 column eluted with a linear gradient of 80% 2-propanol in 0.1% TFA. Selected peptide fractions were subjected to repurification using reversed phase HPLC on another Vydac C18 column eluted with linear gradients of 80% acetonitrile in 0.1% TFA.

N-terminal amino acid sequencing of the intact transglutaminase as well as sequencing of the purified peptides were done in an Applied Biosystems 473A protein sequencer operated according to the manufacturers instructions.

The sequences obtained are shown in the following:

(Xaa designates unidentified residues while Asx designates positions where it could not be determined whether Asp or Asn were present).

N-terminal sequence:
Ala-Ala-Asp-Asp-Arg-Val-Thr-Pro-Pro-Ala-Glu
Peptide 1:
Asp-Asp-Arg-Val-Thr-Pro-Pro-Ala-Glu-Pro-Leu-Asn-Arg-Met
Peptide 2:
Ala-Glu-Phe-Glu-Gly-Arg-Ile-Ala-Lys-Gly-Xaa-Phe
Peptide 3:
Asp-Ala-Phe-Arg-Gly-Phe-Lys-Arg-Ala-Arg-Glu-Val-Ala
Peptide 4:
Asp-His-Leu-Lys-Thr-Glu-Leu-Ala-Asn-Lys
Peptide 5:
Asp-Ser-Arg-Ser-Ser-Phe-Tyr-Ser-Ala-Leu-Arg-Asn-Thr-Pro-Ser-Phe-Lys-Glu-Arg
Peptide 6:
Asp-Pro-Ser-Lys-Met-Lys-Ala-Val-Val-Tyr-Ser-Lys-His-Phe-Trp-Ser-Gly-Gln
Peptide 7:
Asp-Lys-Arg-Lys-Tyr-Gly-Asp-Pro
Peptide 8:
Asp-Tyr-Gly-Trp-Phe-Gly-Ala-Gln-Ala-Glu
Peptide 9:
Asp-Lys-Thr-Val-Trp-Thr-His-Ala-Asx-His-Tyr-His-Ala-Pro-Asx-Gly-Gly-Met-Gly-Pro-Met-Asx-Val
Peptide 10:
Glu-Ser-Lys-Phe-Arg-Asn-Trp-Ser-Ala-Gly-Tyr-Ala
Peptide 11:
Asp-Arg-Gly-Ala-Tyr-Val-Ile-Thr-Phe-Ile-Pro-Lys-Ser-Trp-Asn-Thr-Ala
Peptide 12:
Phe-Phe-Asp-Glu-Asn-Lys
Peptide 13:
Arg-Ala-Arg-Glu-Val-Ala-Ser-Val-Met-Asn-Lys
Peptide 14:
Ala-Leu-Asp-Ser-Ala-His-Asp-Glu-Gly-Thr-Tyr-Ile-Asp-His-Leu-Lys
Peptide 15:
Thr-Glu-Leu-Ala-Asn-Lys
Peptide 16:
Ala-Leu-Arg-Asn-Thr-Pro-Ser-Phe
Peptide 17:
Xaa-Xaa-Asp-Gly-Gly-Asn-Tyr-Asp-Pro-Ser-Lys
Peptide 18:
Ala-Val-Val-Tyr-Ser-Lys
Peptide 19:
His-Phe-Trp-Ser-Gly-Gln-Asp-Pro-Arg-Gly-Ser-Ser-Asp-Lys
Peptide 20:
Tyr-Gly-Asp-Pro-Asp-Ala-Phe-Arg-Pro-Asp-Gln-Gly-Thr-Gly-Leu-Val-Asp-Met-Ser-Arg-Asp-Arg-Asn-Ile-Pro-Arg-Ser-Pro-Ala-Lys
Peptide 21:
Pro-Gly-Glu-Pro-Phe-Val-Asn-Phe-Asp-Tyr-Gly-Trp-Phe-Gly-Ala-Gln-Ala-Glu-Ala-Asp-Ala-Asp-Lys
Peptide 22:
Thr-Val-Trp-Thr-His-Ala-Asn
Peptide 23:
Asn-Trp-Ser-Ala-Gly-Tyr-Ala-Asp-Phe-Asp-Arg-Gly-Ala-Tyr-Val-Ile-Thr-Phe-Ile-Pro-Lys
Peptide 24:
Ser-Trp-Asn-Thr-Ala-Pro-Ala-Glu-Val-Lys
Peptide 25 (C-terminal peptide):
Gln-Gly-Trp-Pro Below the combined sequences are aligned to the sequence of a transglutaminase from Streptoverticillium (Kanaji et al., 1994; Washizu et al., 1994; EP-A-0 481 504). Although the two enzymes are homologous they are clearly different as 19% (46 out of 240) of the residues sequenced from the Streptomyces platensis transglutaminase differ from the corresponding residue in the Streptoverticillium transglutaminase. It should be stressed that many of the substitutions found are non-conservative—e.g. AsplAla, Ser84Phe, Glu115Gly, Glu119Ala, Glu120Phe, Gln124Lys, Asn149His, Lys152Thr, Gly157Lys, Pro169Ser, His188Tyr, Arg208Pro, Ser209Arg, Ala226Asp, Pro227Gln, Ser246Lys, Gly250Pro, Ala287Pro, His289Asx, Glu300Ala, Asp324Ala and Lys325Glu. The first mentioned residue is the one found in the transglutaminase from Streptoverticillium and the second residue is the one found in the transglutaminase from *Streptomyces platensis*:

Alignment of the Combined Peptide Sequences Obtained from *Streptomyces platensis* Transglutaminase to the Amino Acid Sequence of Streptoverticillium Transglutaminase X designates an unidentified residue whereas B designates Asx.

Upper sequence: *Streptomyces platensis* transglutaminase

Lower sequence: Streptoverticillium transglutaminase

Divergence: 46 out of 240 residues sequenced (19%)
Differences are marked with an asterisk (*)

```
            **              *
     AADDRVTPPA  EPLNRM
   1 DSDDRVTPPA  EPLDRMPDPY  RPSYGRAETV  VNNYIRKWQQ  VYSHRDGRKQ

*    **
                                  FFDENK
  51 QMTEEQREWL  SYGCVGVTWV  NSGQYPTNRL  AFASFDEDRF  KNELKNGRPR

*    *     **  *    *           *   **     **  *   *
         AEFEG  RIAKGXFDAF  RGFKRAREVA  SVMNKALDSA  HDEGTYIDHL
 101 SGETRAEFEG  RVAKESFDEE  KGFQRAREVA  SVMNRALENA  HDESAYLDNL

*    *              *    *                *    *    *   *
     KTELANK        DSRSSF  YSALLNTPSF  KERDGGNYDP  SKMKAVVYSK
 151 KKELANGNDA  LRNEDARSPF  YSALRNTPSF  KERNGGNHDP  SRMKAVIYSK

***  *                 **                      **   *
     HFWSGQDPRG  SSDKRKYGDP  DAFRPDQGTG  LVDMSRDRNI  PRSPAKPGEP
 201 HFWSGQDRSS  SADKRKYGDP  DAFRPAPGTG  LVDMSRDRNI  PRSPTSPGEG

*           *          ** *  *              *
     FVNFDYGWFG  AQAEADADKT  VWTHANHYHA  PBGGMGPMBV    ESKFRNWSA
 251 FVNFDYGWFG  AQTEADADKT  VWTHGNHYHA  PNGSLGAMHV  YESKFRNWSE

*                         **
     GYADFDRGAY  VITFIPKSWN  TAPAEVKQGW  P
 301 GYSDFDRGAY  VITFIPKSWN  TAPDKVKQGW  P           331
```

EXAMPLE 12

*Streptomyces lydicus* Transglutaminase—pH and Temperature Optimum and Immunological Cross-reactivity with Transglutaminase from *Streptomyces mobaraense*

Enzyme assays

Putrescine assay

The putrescine assay was in principle performed according to Lorand et al. (1972).

The reaction mixture contained: 50 nmoles of [$^{14}$C]-putrescine (4.03 GBq/mmol; Amersham), 6 mg of α-casein (dephosporylated, Sigma no. C-8032), 5 μmoles of glutathione, and 5–10 μg of TGase made up to 1 ml with 0.2 M Tris-HCl, pH 7.9 or 40 mM Britton-Robinson buffer at the relevant pH. The incubations were performed at ambient temperature. Aliquots of 30 μl were withdrawn after 1 and 2 h, respectively, and spotted onto Whatman 3 MM filters (D=2 cm). The filters were immediately put into a basket submerged in ice-cold 10% TCA and washed for 20 min. Following the first wash the filters were washed three times with ice-cold 5% TCA, two times with ice-cold acetone. In each washing step there should be at least 5 ml of washing solution per filter. The filters were dried, put into counting vials containing 8 ml of scintillation fluid (Optiphase, Wallac) and the radioactivity was measured in a Packard Tri-Carb liquid scintillation spectrometer. Each determination was performed in triplicate.

Hydroxamate assay

The hydroxamate assay was in principle performed as described by Folk and Cole (1965). The stop reagent was made of equal volumes of 15% acetic acid, 5% FeCl$_3$, and 2.5 N HCl.

The reaction mixture contained: 5 μmoles of glutathione, 100 μmoles of hydroxylamine chloride, 30 μmoles of CBZ-Gln-Gly and 0.1 mg TGase made up to 1 ml with 40 mM Britton-Robinson buffer, pH 7.5. The incubations were performed at different temperatures and stopped after 20 min of incubation by addition of an equal volume of stop reagent. The absorbance at 490 nm was measured in an UV$_{max}$ kinetic microplate reader.

The temperature optimum for the *S. lydicus* TGase was measured in the hydroxamate assay and optimum was found to be 50° C. The results were:

| Temp (° C.) | Relative activity (%) |
|---|---|
| 30 | 30 |
| 40 | 75 |
| 45 | 90 |
| 50 | 100 |
| 55 | 75 |
| 60 | 20 |
| 70 | 10 |

The pH profile for the *S. lydicus* TGase was determined in the putrescine assay varying pH from 6 to 9. Optimum was found to be around pH 8. The results were:

| pH | Relative activity (%) |
|---|---|
| 6.0 | 6 |
| 6.5 | 12 |
| 7.0 | 21 |
| 7.5 | 40 |
| 8.0 | 57 |
| 8.5 | 83 |
| 9.0 | 100 |

The TGase from *S. lydicus* was analyzed for immunological cross-reactivity with the TGase from *Streptoverticillium mobaraense*. A polyclonal antibody was raised against the pure *S. mobaraense* enzyme and using an Ouchterlony immunodiffusion assay there was found to be no cross-reactivity between the TGases from *S. lydicus* and *S. mobaraense*.

Experimental

Four rabbits were immunized with the pure TGase from *S. mobaraense* according to standard procedures. The antiserum from all four rabbits was pooled and the antibody was purified on a HiTrap Protein G column from Pharmacia following the recommended procedure. The purified antibody was used in an ouchterlony immunodiffusion (1% agarose in 0.1 M Tris-HCl) using the pure TGases from *S. mobaraense* and *S. lydicus* as antigens.

EXAMPLE 13
Fermentation and Production of TGase from *Streptomyces lydicus*, NRRL B-3446 (Former *Streptomyces libani*)

The strain was grown in a 2 liter fermentation vessel supplied with a magnetic coupled stirrer drive, pH- and temperature control and a peristaltic pump to add the carbon source at fixed rates. After growth for 3 days on a YPG agarslant at 30° C. a lump of the mycelium was inoculated in to a 500 ml shakeflask containing a YPD-broth(2% yeast extract, 1% Bacto peptone, 6% glucose) and propagated for 24 hours at 250 rpm and 30° C. 100 ml of this culture was used to inoculate the fermentor already containing 1,3 liter broth with the following ingredients:

| | | |
|---|---|---|
| Yeast extract, 50%: | 60 g | |
| Amicase: | 30 g | |
| $MgS_2SOO_4.7H_2O$: | 3 g | |
| $K_2SO_4$: | 4 g | |
| Trace metals: | 3 ml | |
| Vitamin I: | 1.5 ml | |
| Vitamin II: | 1.5 ml | |
| Pluronic (antifoam): | 3 ml | |

Volume adjusted to 1.3 liters with tap water. pH adjusted to 7.0 before sterilization in an autoclave at 121° C. for 60 minutes. Also a glucose solution was separately made in a 1 liter flask containing 250 g of glucose, $1H_2O$ and 0.25 grams of citric acid in tapwater. Volume adjusted to 500 ml before autoclaving as above.

Biomass Growth and Enzyme Formation

After inoculation of the culture as descibed above the glucose solution was fed at a constant rate (9 g/h) to the fermentor over the next 17 hours. A peristaltic Watson-Marlow pump was used. Also sterile filtered air was sparged into the fermentor at the bottom drive at a rate of 1.4 liter/minute and this rate was kept throughout the fermentation. The stirrer speed was at the beginning set to 300 rpm, but automatically coupled to the dissolved oxygen tension signal and a setpoint of 10% DOT and therefore running close to the maximum value of 1100 rpm after 17 hours. The glucose feed rate was now increased to 14.5 grams/hour, which was kept over the next 24 hours and finishing the glucose reservoir. During this period stirrer speed was at the maximum (1150 rpm) and DOT close to zero. A surplus of glucose was also present and this was diminished to ~0.1% glucose over the next 7 hours. Temperature was controlled at 30.0+/−0.1° C. and pH to 7.00+/−0.05 by addition of diluted ammonia in water.

After these 48 hours of growth the culture, with a biomass of 45 g of dry biomass per liter, was harvested and the very viscous mycelium nearly quantitatively removed by addition of 500 ml of tap water. The suspension was stored in the cold (4° C.) for 3 days. The supernatant was removed after centrifugation 30 minutes at 4000 rpm. The precipitate was diluted to the original volume in tap water, suspended and again centrifuged, now for 45 minutes. Enzyme concentrations in the two supernatants were determined by the hydroxamate assay.

Yields are shown in the table below:

| | Quantity, grams | Yield of TGase, mg/l | Yield of TGase, mg |
|---|---|---|---|
| Diluted broth | 1993 | | |
| Supernatant I | 1536 | 120 | 184 |
| Supernatant II | 1675 | 50 | 84 |
| Total | | | 268 |

This yield corresponds to ~180 mg/l undiluted broth.

This should be compared with the prior art yields of transglutaminase reported to be not higher than about 2.47 units/ml in the hydroxamate assay, see U.S. Pat. No. 5,252,469.

| Trace metal solution. | |
|---|---|
| Conc. HCl | 5 ml |
| $ZnCl_2$ | 3.4 g |
| $FeCl_3.6H_2O$ | 27 g |
| $MnCl2.4H_2O$ | 9.55 g |
| $CuSO4.5H_2O$ | 1.1 g |
| $CoCl_2$ | 1.29 g |
| $H_3BO_3$ | 0.31 g |
| $(NH_4)6Mo_7O_{24}.4H_2O$ | 0.1 g |
| Destilled water at | 1000 ml |
| Vitamin I | |
| Biotin | 1,25 g |
| Thiamin | 20 g |
| D-calciumpanthotenate | 250 g |
| Myoinositol | 500 g |
| Cholinchloride | 500 g |
| Pyridoxin | 16 g |
| Niacinamide | 12 g |
| Folicacid | 2 g |
| Destilled water at | 10 l |
| Vitamin II | |
| Riboflavine | 4 g |
| Destilled water at | 10 l |

EXAMPLE 14
Viscosity Increase in Na-caseinate Solution

A solution of Na-caseinate (Miprodan 30, MD Foods, Denmark) was prepared containing 9% protein. pH was adjusted to 7.0 using NaOH.

Viscosity was measured using the Sofraser MIVI 2000 viscosimeter. Viscosity reading is given as mV setting the set point to 0 mV when measuring wihtout enzyme addition.

The experiment compared two transglutaminases:
1. Commerciel transglutaminase (Ajinomoto TG-K) which is formulated with dextrin 24%, Ca-lactate 75% and enzyme 1%.
2. Freeze dried enzyme preparation from *Streptomyces lydicus*, NRRL B-3446 (former *Streptomyces libani*) fermentation.

Activity of both enzymes are measured by the hydroxamate assay as described in EP 0379606 A1. Based upon this the dosage for both enzymes were 0,36 mg enzyme for a 5 ml substrate solution.

The experiment was carried out twice at 50° .C and 55° C., respectively, and the results are shown in the tables below.

| Measurement (mV) at 50° C.: | | |
|---|---|---|
| Time, minutes | TG-K | Streptomyces lydicus |
| 0 | 0 | 0 |
| 6 | 110 | 147 |
| 11 | 64 | 161 |
| 15 | 70 | 173 |
| 20 | 130 | 300 |
| 25 | 240 | 439 |
| 30 | 323 | 561 |
| 35 | 333 | 612 |
| 40 | 390 | 728 |
| 45 | 514 | 833 |
| 50 | 813 | 947 |
| 55 | 1142 | 992 |
| 60 | 1374 | 1040 |
| 65 | 1416 | 1097 |
| 70 | 1230 | 1160 |
| 75 | 1269 | 1196 |

| Measurement (mV) at 55° C.: | | |
|---|---|---|
| Time, minutes | TG-K | Streptomyces lydicus |
| 0 | 0 | 0 |
| 5 | 108 | 55 |
| 10 | 133 | 175 |
| 15 | 233 | 289 |
| 25 | 329 | 468 |
| 30 | 399 | 602 |
| 40 | 477 | 691 |
| 50 | 661 | 784 |
| 60 | 596 | 873 |
| 70 | 745 | 895 |
| 75 | 720 | 892 |

Both enzymes show activity at 50° C. and 55° C. The results shows that the activity of *Streptomyces lydicus*, NRRL B-3446 (former *Streptomyces libani*) transglutaminase is higher at 55° C. compared to the TG-K transglutaminase indicating a higher temperature optimum and/or higher thermostability for the *Streptomyces lydicus*, NRRL B-3446 (former *Streptomyces libani*) enzyme.

EXAMPLE 15
Gene Encoding the Transglutaminase from *Streptomyces lydicus*
Materials and Methods
Donor Organism DNA was isolated from *Streptomyces lydicus*, NRRL B-3446. The used host was *E. coli* SJ2 (Diderichsen, B. et al., (1990)).
Plasmid The gene bank vector was pSJ1678 which is further disclosed in WO94/19454 which is hereby incorporated by reference. The cloning vector was pPL1759.

Chromosomal DNA from *Streptomyces lydicus*, NRRL B-3446, was partial digested with the restriction enzyme Sau3A1. The fragments were cloned into the BamHI sites of a clonings vector pSJ1678, cf. FIG. 1 and WO 95/01425, and transformed into *Escherichia coli* SJ2 (Diderichsen, B. et al., (1990)), thereby creating a gene library of *S.lydicus*.

From the protein sequence made by sequencing the *S.lydicus* transglutaminase protein two PCR primers were predicted. A primer containing a PstI site and the predicted 30 bases of the 5'-terminal (primer 7854) and a primer containing a restriction enzyme HindIII recognition sequence and 30 bases complementary to the predicted transglutaminase 3' sequence (primer 7855) of the mature transglutaminase gene from *S.lydicus* was prepared:

7854 :
5'-CCTCATTCTGCAGCAGCGGCGGCAGCCGACGA AAGGGTCACCCCTCCCGCC-3'
7855 :
5'-GCGCGAAGCTTCACGACCAGCCCTGCTTTACC TCGGCGGGGGC-3'

2–4 mg Chromosomal DNA from *S.lydicus* was used as template in a PCS reaction (20 cycles) using the primers 7854 and 7855 and Super Taq DNA polymerase and following the manufacturer's instructions (Super Taq™ DNA polymerase/PCR buffer, HT BIOTECHNOLOGY LTD).

A PCR fragment corresponding to the expected size of the transglutaminase from *S.lydicus* was recovered from an agarose gel and digested with the restriction enzymes HindIII and PstI.

Figure 2:
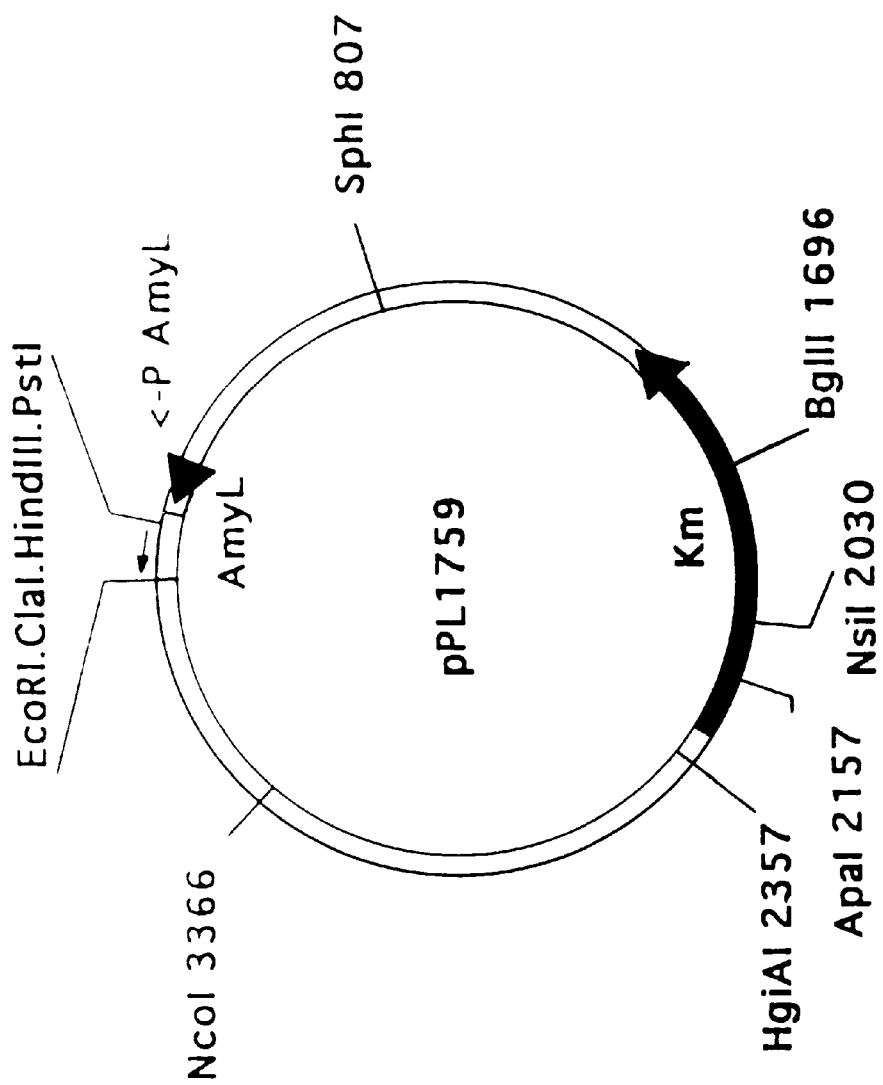
FIG. 2 is a schematic representation of a plasmid designated pPL1759.

The plasmid pPL1759, see FIG. 2 and Hansen, C. (1992), was digested with the restriction enzymes PstI-HindIII and the large vector fragment was ligated to the PCR fragment. Ligation mixture was transformed into *Bacillus subtilis* DN1885 (P.L.Jørgensen et al., (1990)).

Figure 3:
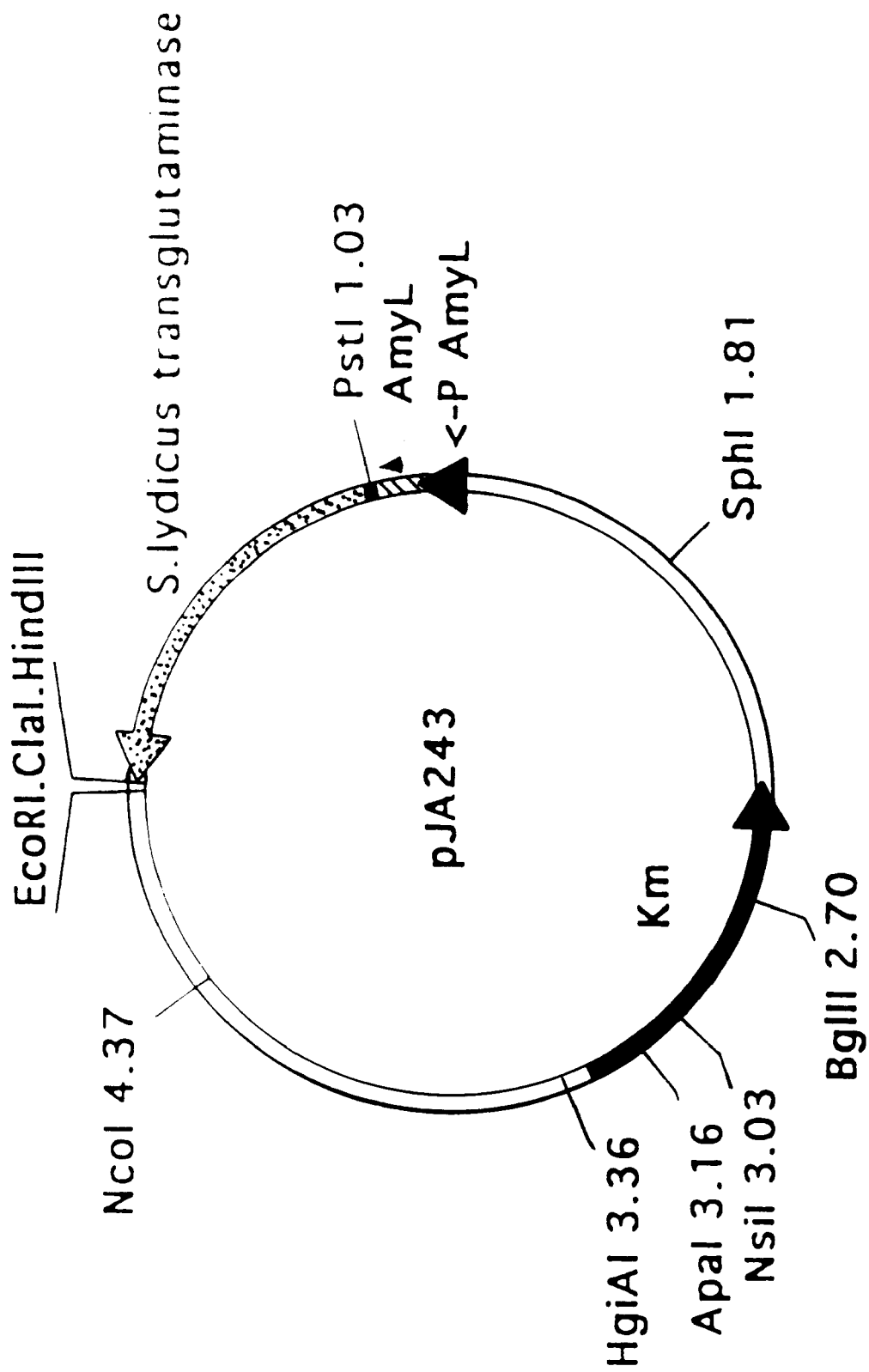
FIG. 3 is a schematic representation of a plasmid designated pJA243.

Selection for transformants and reisolation of those was performed on LBPG media with 10 μg Kanamycin/ml. DNA analysis of the plasmids from those clones using a DNA sequencing Kit (SEQUENASE™ (United States Biochemicals)) showed the expected sequence (SEQ ID NO. 1) of the mature transglutaminase encoding region when it was translated and compared to the partial sequenced transglutaminase protein of *S.lydicus*. This plasmid was termed pJA243 and a *B. subtilis* DN1885 strain harbouring this plasmid was termed JA243. A plasmid map of pJA243 is shown in FIG. 3.

The PstI-HindIII fragment of pJA243 was used as template for making a radioactive labeled probe using the Nick Translation Kit™ as described by the manufacturer (code N.5500 from Amersham). This radioactive probe was used for colony hybridization to the gene bank of *S.lydicus*. To find the native transglutaminase gene a positive clone was isolated. This bacterium contained a fragment inserted in plasmid pSJ1678. The cloned DNA could be amplified with the primers 7854 and 7855 giving a fragment of the correct size. The clone was denoted JA260 and deposited under the Budapest Treaty on Aug. 23, 1995 as DSM 10175 (*E. coli*).

EXAMPLE 16
Inhibition of Bacterial TGases with PMSF (Phenyl Methyl Sulfonyl Fluoride)

A putrescine control assay was performed to investigate whether TGases from different bacterial strains are sensitive to PMSF (phenyl methyl sulfonyl fluoride). The purified transglutaminases from *S. lydicus* and *S. mobaraense* was found to be insensitive to PMSF.

The assay was run under optimized conditions (see examples 1–3), i.e. 1 h incubation at 30° C., pH 8.5 (2% α-casein+EDTA in 100 mM modified Britton-Robinson-buffer 0.1 M, pH 8.5). Final concentration of PMSF was 1.6 mM. As control an assay including propanol was included: propanol is the solvent of PMSF. This assay ensures that solvent effects are excluded. The assay contained 0.9 M 2-propanol i.e. the same concentration as in PMSF containing assay (addition of 8 41 propanol from 13 M instead of 8 μl PMSF in 2-propanol).

Results

| Strain | Relative activity (%) | |
|---|---|---|
| | −PMSF | +PMSF |
| Bacteridium (DSM 10093) | 100 | 75 |
| Bacteridium (CBS 495.74) | 100 | 75 |
| Moo5A10 | 100 | 75 |
| Bacillus badius | 100 | 62 |
| Bacillus firmus | 100 | 55 |
| Bacillus mycoides | 100 | 35 |
| B. aneurinolyticus | 100 | 47 |
| S. lydicus | 100 | 175 |

TGase activity of all strains investigated except S. lydicus was inhibited by the addition of PMSF: Bacillus badius, Bacillus firmus, Bacillus mycoides, Bacillus aneurinolyticus, strain Moo5A10, Bacteridium (DSM10093) and Bacteridium (CBS 495.74).

This result is in contrast to the TGase from Streptomyces lydicus and the known microbial transglutaminases. This result implies that the PMSF-sensitive TGases listed above possess different catalytic active sites than the TGases from Streptomyces and all other known TGases (including Factor XIII).

EXAMPLE 17
Gelling of Skimmilk with Bacterial TGases
Experimental

150 μl of skimmilk solutions (15 and 20 %) and 50 μl of supernatant (i.e. different TGase activities) were incubated in Eppendorf Tubes at 30° C. while shaking with 700 rpm on a thermostated shaker.

Assays were visibly controlled every hour and after over night incubation (about 18 h). Samples used were centricon treated (in order to eliminate $Ca^{2+}$-ions): corresponding samples (1 ml) were concentrated in a 10 kDa Centricon tube (no TGase activity in the filtrate), resuspended with $Ca^{2+}$-free Tris-buffer (0.1 M, pH 7.5) up to 1 ml, centrifuged again and concentrated by resuspending the retentate in 0.25 ml of Tris buffer.

Controls: As some of the media used contain high concentrations of $Ca^{2+}$ (Medium H: 34 mM; Medium K nd Q: 3.4 mM; Medium L: 13.6 mM) controls were run to check $Ca^{2+}$-dependent (Tgase-independent) effects. The media were treated as described for the samples with centricon tubes.

Results

All strains investigated showed a gelling of 15 and/or 20% skimmilk:

Bacteridium (2 strains), Bacillus firmus, Bacillus mycoides, Bacillus badius, Bacillus aneurinolytikus, strain Moo5A10 and Rothia dentocariosa. Bacillus mycoides and Bacillus aneurinolyticus showed positive effects after 60 minutes of incubation, all others were positive after over night incubation.

References

Klein et al., Journal of Bacteriology, Vol. 174, pages 2599–2605, (1992).

U.S. Pat. No. 5,156,956 (Motoki et al.)
U.S. Pat. No. 5,252,469 (Andou et al.).
Kaempfer et al., Journal of General Microbiology, Vol. 137, pages 1831–1892, (1991).
Ochi et al., International Journal of Systematic Bacteriology, Vol. 44, pages 285–292, (1994).
Williams et al., Journal of General Microbiology, Vol. 129, pp. 1743–1813.
Washizu et al., Bioscience, Biotechnology and Biochemistry Vol. 58, pages 82–87, (1994).
Tahekana et al., ibid. Vol. 58, pages 88–92.
EP-0 481 504 A1 (Takagi et al.).
U.S. Pat. No. 5,252,469.
Sambrook, J., Fritsch, E. F. & Maniatis, T. 1989. Molecular Cloning: A Laboratory Manual. Cold Spring Harbor Lab., Cold Spring Harbor, N.Y.
Ford et al., Protein Expression and Purification 2: 95–107, 1991.
Cunningham and Wells, Science 244, 1081–1085, (1989).
dè Vos et al., Science 255: 306–312, (1992).
Smith et al., J. Mol. Biol. 224: 899–904, 1992.
Wlodaver et al., FEBS Lett. 309: 59–64, 1992.
N. Axelsen et al., A Manual of Quantitative Immunoelectrophoresis, Blackwell Scientific Publications, 1973, Chapters 2,3,4 and 23.
Needleman, S. B. and Wunsch, C. D., Journal of Molecular Biology, 48: 443–453, 1970
WO 94/14953
U.S. Pat. NO. 4,683,202
Saiki, R. K. et al., (1988), Science 239, p. 487–491.
Beaucage and Caruthers, (1981), Tetrahedron Letters 22, p. 1859–1869.
Matthes et al., (1984), EMBO Journal 3, p. 801–805.
EP-A-0 238 023
A. Johnstone and R. Thorpe, Immunochemistry in Practice, Blackwell Scientific Publications, 1982 (more specifically pp. 27–31).
O. Ouchterlony in: Handbook of Experimental Immunology (D. M. Weir, Ed.), Blackwell Scientific Publications, 1967, pp. 655–706.
WO 95/01425
Diderichsen, B., Wedsted, U., Hedegaard, L., Jensen, B. R., Sjøholm, C., Journal of Bacteriology, Vol. 172, No. 8, p. 4315–4321, (1990).
W094/19454
Hansen, C. (1992) PhD Thesis, The Technical University of Denmark
P. L. Jørgensen et al., Gene (1990) 96, 37–41
Folk, J. E. & Cole, P. W. (1966), J. Biol. Chem. 241, 5518–5525
EP-A-0 481 504
Curtis, C. G. & Lorand, L. (1976), Methods in Enzymology 45, 177–191
Kanaji et al., J. Biol. Chem. 268, 11565–11572, 1994.
Lorand, L., Campbell-Wilkes, L. K., and Cooperstein, L. (1972), Anal. Biochem., 50, 623–631
Folk, J. E., and Cole, P. W. (1965) J. Biol. Chem., 240, 2951

What is claimed is:

1. A method for identifying a transglutaminase-producing microorganism, said method comprising:
   a) cultivating a microorganism in a liquid culture to obtain a culture broth;
   b) measuring the ability of the broth to catalyze incorporation of putrescine into casein;
   c) measuring the ability of the broth to catalyze conversion of hydroxylamine to hydroxamic acid; and
   d) selecting microorganisms wherein the broth (i) catalyzes incorporation of putrescine into casein and (ii) does not catalyze the conversion of hydroxylamine to hydroxamic acid.

2. A method for polymerizing α-casein, said method comprising contacting said casein with an isolated transglutaminase produced by a microorganism that is identified using a method as defined in claim 1, under conditions suitable for polymerization.

3. A method for gelling protein, said method comprising contacting said protein with an isolated transglutaminase produced by a microorganism that is identified using a method as defined in claim 1, under conditions suitable for gelling.

4. A method for preparing cheese, said method comprising contacting milk concentrate with an isolated transglutaminase produced by a microorganism that is identified using a method as defined in claim 1, under conditions suitable for forming cheese.

5. A method for improving the baking quality of flour, said method comprising contacting said flour with an isolated transglutaminase produced by a microorganism that is identified using a method as defined in claim 1, under conditions suitable for improving the quality of said flour.

6. A method for producing paste-type food products, said method comprising contacting protein, fat, and water with an isolated transglutaminase produced by a microorganism that is identified using a method as defined in claim 1, under conditions suitable for paste formation.

7. A method for improving the taste and/or texture of a food product, said method comprising contacting said food product with an isolated transglutaminase produced by a microorganism that is identified using a method as defined in claim 1, under conditions suitable for improving the taste and/or texture of said product.

8. A method for processing leather, said method comprising contacting said leather with an isolated transglutaminase produced by a microorganism that is identified using a method as defined in claim 1, under conditions suitable for said processing.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 993 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Streptomyces lydicus
      (C) INDIVIDUAL ISOLATE: NRRL B-3446

(ix) FEATURE:
      (A) NAME/KEY: CDS
      (B) LOCATION: 1..993

(xi) SEQUENCE DESCRIPTION: SEQ ID NO: 1:

```
GCA GCC GAC GAA AGG GTC ACC CCT CCC GCC GAG CCG CTC AAC CGG ATG      48
Ala Ala Asp Glu Arg Val Thr Pro Pro Ala Glu Pro Leu Asn Arg Met
 1               5                  10                  15

CCT GAC GCG TAC CGG GCC TAC GGA GGT AGG GCC ACT ACG GTC GTC AAC      96
Pro Asp Ala Tyr Arg Ala Tyr Gly Gly Arg Ala Thr Thr Val Val Asn
             20                  25                  30

AAC TAC ATA CGC AAG TGG CAG CAG GTC TAC AGT CAC CGC GAC GGC ATC     144
Asn Tyr Ile Arg Lys Trp Gln Gln Val Tyr Ser His Arg Asp Gly Ile
         35                  40                  45

CAA CAG CAA ATG ACC GAA GAG CAG CGA GAA AAG CTG TCC TAC GGC TGC     192
Gln Gln Gln Met Thr Glu Glu Gln Arg Glu Lys Leu Ser Tyr Gly Cys
     50                  55                  60

GTC GGC ATC ACC TGG GTC AAT TCG GGC CCC TAC CCG ACG AAT AAA TTG     240
Val Gly Ile Thr Trp Val Asn Ser Gly Pro Tyr Pro Thr Asn Lys Leu
 65                  70                  75                  80

GCG TTC GCG TTC TTC GAC GAG AAC AAG TAC AAG AGT GAC CTG GAA AAC     288
Ala Phe Ala Phe Phe Asp Glu Asn Lys Tyr Lys Ser Asp Leu Glu Asn
                 85                  90                  95

AGC AGG CCA CGC CCC AAT GAG ACG CAA GCC GAG TTT GAG GGG CGC ATC     336
Ser Arg Pro Arg Pro Asn Glu Thr Gln Ala Glu Phe Glu Gly Arg Ile
            100                 105                 110

GTC AAG GAC AGT TTC GAC GAG GGG AAG GGT TTC AAG CGG GCG CGT GAT     384
Val Lys Asp Ser Phe Asp Glu Gly Lys Gly Phe Lys Arg Ala Arg Asp
        115                 120                 125

GTG GCG TCC GTC ATG AAC AAG GCC CTG GAT AGT GCG CAC GAC GAG GGG     432
Val Ala Ser Val Met Asn Lys Ala Leu Asp Ser Ala His Asp Glu Gly
    130                 135                 140

ACT TAC ATC GAC AAC CTC AAG ACG GAG CTC GCG AAC AAA AAT GAC GCT     480
Thr Tyr Ile Asp Asn Leu Lys Thr Glu Leu Ala Asn Lys Asn Asp Ala
145                 150                 155                 160

CTG CGC TAC GAG GAC GGT CGC TCG AAC TTT TAC TCG GCG CTG AGG AAT     528
Leu Arg Tyr Glu Asp Gly Arg Ser Asn Phe Tyr Ser Ala Leu Arg Asn
                165                 170                 175

ACG CCG TCC TTC AAG GAA AGG GAT GGA GGT AAC TAC GAC CCA TCC AAG     576
Thr Pro Ser Phe Lys Glu Arg Asp Gly Gly Asn Tyr Asp Pro Ser Lys
            180                 185                 190

ATG AAG GCG GTG GTC TAC TCG AAA CAC TTC TGG AGC GGG CAG GAC CAG     624
Met Lys Ala Val Val Tyr Ser Lys His Phe Trp Ser Gly Gln Asp Gln
        195                 200                 205
```

```
CGG GGC TCC TCT GAC AAG AGG AAG TAC GGC GAC CCG GAT GCC TTC CGC      672
Arg Gly Ser Ser Asp Lys Arg Lys Tyr Gly Asp Pro Asp Ala Phe Arg
210             215                 220

CCC GAC CAG GGC ACA GGC CTG GTA GAC ATG TCG AAG GAC AGG AAT ATT      720
Pro Asp Gln Gly Thr Gly Leu Val Asp Met Ser Lys Asp Arg Asn Ile
225             230                 235                 240

CCG CGC AGT CCC GCC CAA CCT GGC GAA AGT TGG GTC AAT TTC GAC TAC      768
Pro Arg Ser Pro Ala Gln Pro Gly Glu Ser Trp Val Asn Phe Asp Tyr
                245                 250                 255

GGC TGG TTT GGG GCT CAG ACG GAA TCG GAC GCC GAC AAA ACC ATA TGG      816
Gly Trp Phe Gly Ala Gln Thr Glu Ser Asp Ala Asp Lys Thr Ile Trp
            260                 265                 270

ACC CAC GCC AAC CAC TAT CAC GCG CCC AAC GGC GGC CTG GGC CCC ATG      864
Thr His Ala Asn His Tyr His Ala Pro Asn Gly Gly Leu Gly Pro Met
                275                 280                 285

AAC GTA TAT GAG AGC AAG TTC CGG AAC TGG TCT GCC GGG TAC GCG GAT      912
Asn Val Tyr Glu Ser Lys Phe Arg Asn Trp Ser Ala Gly Tyr Ala Asp
290                 295                 300

TTC GAC CGC GGA ACC TAC GTC ATC ACG TTC ATA CCC AAG AGC TGG AAC      960
Phe Asp Arg Gly Thr Tyr Val Ile Thr Phe Ile Pro Lys Ser Trp Asn
305             310                 315                 320

ACC GCC CCC GCC GAG GTA AAG CAG GGC TGG TCG                          993
Thr Ala Pro Ala Glu Val Lys Gln Gly Trp Ser
                325                 330

(2) INFORMATION FOR SEQ ID NO: 2:

(i) SEQUENCE CHARACTERISTICS:
        (A) LENGTH: 331 amino acids
        (B) TYPE: amino acid
        (D) TOPOLOGY: linear (ii) MOLECULE TYPE: protein (xi) SEQUENCE DESCRIPTION: SEQ ID NO: 2:

Ala Ala Asp Glu Arg Val Thr Pro Pro Ala Glu Pro Leu Asn Arg Met
1               5                   10                  15

Pro Asp Ala Tyr Arg Ala Tyr Gly Gly Arg Ala Thr Thr Val Val Asn
            20                  25                  30

Asn Tyr Ile Arg Lys Trp Gln Gln Val Tyr Ser His Arg Asp Gly Ile
        35                  40                  45

Gln Gln Gln Met Thr Glu Glu Gln Arg Glu Lys Leu Ser Tyr Gly Cys
    50                  55                  60

Val Gly Ile Thr Trp Val Asn Ser Gly Pro Tyr Pro Thr Asn Lys Leu
65              70                  75                  80

Ala Phe Ala Phe Phe Asp Glu Asn Lys Tyr Lys Ser Asp Leu Glu Asn
                85                  90                  95

Ser Arg Pro Arg Pro Asn Glu Thr Gln Ala Glu Phe Glu Gly Arg Ile
            100                 105                 110

Val Lys Asp Ser Phe Asp Glu Gly Lys Gly Phe Lys Arg Ala Arg Asp
        115                 120                 125

Val Ala Ser Val Met Asn Lys Ala Leu Asp Ser Ala His Asp Glu Gly
    130                 135                 140

Thr Tyr Ile Asp Asn Leu Lys Thr Glu Leu Ala Asn Lys Asn Asp Ala
145                 150                 155                 160

Leu Arg Tyr Glu Asp Gly Arg Ser Asn Phe Tyr Ser Ala Leu Arg Asn
                165                 170                 175

Thr Pro Ser Phe Lys Glu Arg Asp Gly Gly Asn Tyr Asp Pro Ser Lys
```

```
                    180                185                190
Met Lys Ala Val Val Tyr Ser Lys His Phe Trp Ser Gly Gln Asp Gln
                195                200                205

Arg Gly Ser Ser Asp Lys Arg Lys Tyr Gly Asp Pro Asp Ala Phe Arg
    210                215                220

Pro Asp Gln Gly Thr Gly Leu Val Asp Met Ser Lys Asp Arg Asn Ile
225                230                235                240

Pro Arg Ser Pro Ala Gln Pro Gly Glu Ser Trp Val Asn Phe Asp Tyr
            245                250                255

Gly Trp Phe Gly Ala Gln Thr Glu Ser Asp Ala Asp Lys Thr Ile Trp
                260                265                270

Thr His Ala Asn His Tyr His Ala Pro Asn Gly Gly Leu Gly Pro Met
            275                280                285

Asn Val Tyr Glu Ser Lys Phe Arg Asn Trp Ser Ala Gly Tyr Ala Asp
            290                295                300

Phe Asp Arg Gly Thr Tyr Val Ile Thr Phe Ile Pro Lys Ser Trp Asn
305                310                315                320

Thr Ala Pro Ala Glu Val Lys Gln Gly Trp Ser
                325                330
```

(2) INFORMATION FOR SEQ ID NO:3:

(i) SEQUENCE CHARACTERISTICS:
        (A) LENGTH: 331 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Asp Ser Asp Asp Arg Val Thr Pro Pro Ala Glu Pro Leu Asp Arg Met
1               5                  10                 15

Pro Asp Pro Tyr Arg Pro Ser Tyr Gly Arg Ala Glu Thr Val Val Asn
            20                 25                 30

Asn Tyr Ile Arg Lys Trp Gln Gln Val Tyr Ser His Arg Asp Gly Arg
        35                 40                 45

Lys Gln Gln Met Thr Glu Glu Gln Arg Glu Trp Leu Ser Tyr Gly Cys
    50                 55                 60

Val Gly Val Thr Trp Val Asn Ser Gly Gln Tyr Pro Thr Asn Arg Leu
65              70                 75                  80

Ala Phe Ala Ser Phe Asp Glu Asp Arg Phe Lys Asn Glu Leu Lys Asn
                85                 90                 95

Gly Arg Pro Arg Ser Gly Glu Thr Arg Ala Glu Phe Glu Gly Arg Val
            100                105                110

Ala Lys Glu Ser Phe Asp Glu Glu Lys Gly Phe Gln Arg Ala Arg Glu
        115                120                125

Val Ala Ser Val Met Asn Arg Ala Leu Glu Asn Ala His Asp Glu Ser
    130                135                140

Ala Tyr Leu Asp Asn Leu Lys Lys Glu Leu Ala Asn Gly Asn Asp Ala
145                150                155                160

Leu Arg Asn Glu Asp Ala Arg Ser Pro Phe Tyr Ser Ala Leu Arg Asn
                165                170                175

Thr Pro Ser Phe Lys Glu Arg Asn Gly Gly Asn His Asp Pro Ser Arg
            180                185                190

Met Lys Ala Val Ile Tyr Ser Lys His Phe Trp Ser Gly Gln Asp Arg
```

```
                    195                 200                 205
Ser Ser Ser Ala Asp Lys Arg Lys Tyr Gly Asp Pro Asp Ala Phe Arg
        210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
                260                 265                 270

Thr His Gly Asn His Tyr His Ala Pro Asn Gly Ser Leu Gly Ala Met
                275                 280                 285

His Val Tyr Glu Ser Lys Phe Arg Asn Trp Ser Glu Gly Tyr Ser Asp
        290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330
```

(2) INFORMATION FOR SEQ ID NO: 4:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
       (A) ORGANISM: Streptomyces platensis (xi) SEQUENCE DESCRIPTION: SEQ ID NO: 4:

```
Ala Ala Asp Asp Arg Val Thr Pro Pro Ala Glu Pro Leu Asn Arg Met
1               5                   10                  15
```

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 5:

```
Phe Phe Asp Glu Asn Lys
1               5
```

(2) INFORMATION FOR SEQ ID NO: 6:

(i) SEQUENCE CHARACTERISTICS:
        (A) LENGTH: 52 amino acids
        (B) TYPE: amino acid (C) STRANDEDNESS:
          (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 6:

```
Ala Glu Phe Glu Gly Arg Ile Ala Lys Gly Xaa Phe Asp Ala Phe Arg
1               5                   10                  15

Gly Phe Lys Arg Ala Arg Glu Val Ala Ser Val Met Asn Lys Ala Leu
            20                  25                  30

Asp Ser Ala His Asp Glu Gly Thr Tyr Ile Asp His Leu Lys Thr Glu
            35                  40                  45

Leu Ala Asn Lys
        50
```

(2) INFORMATION FOR SEQ ID NO: 7:

(i) SEQUENCE CHARACTERISTICS:
        (A) LENGTH: 126 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 7:

```
Asp Ser Arg Ser Ser Phe Tyr Ser Ala Leu Arg Asn Thr Pro Ser Phe
1               5                   10                  15

Lys Glu Arg Asp Gly Gly Asn Tyr Asp Pro Ser Lys Met Lys Ala Val
            20                  25                  30

Val Tyr Ser Lys His Phe Trp Ser Gly Gln Asp Pro Arg Gly Ser Ser
            35                  40                  45

Asp Lys Arg Lys Tyr Gly Asp Pro Asp Ala Phe Arg Pro Asp Gln Gly
        50                  55                  60

Thr Gly Leu Val Asp Met Ser Arg Asp Arg Asn Ile Pro Arg Ser Pro
65                  70                  75                  80

Ala Lys Pro Gly Glu Pro Phe Val Asn Phe Asp Tyr Gly Trp Phe Gly
                85                  90                  95

Ala Gln Ala Glu Ala Asp Ala Asp Lys Thr Val Trp Thr His Ala Asn
                100                 105                 110

His Tyr His Ala Pro Asx Gly Gly Met Gly Pro Met Asx Val
            115                 120                 125
```

(2) INFORMATION FOR SEQ ID NO: 8:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: peptide (iii) HYPOTHETICAL: NO -continued (iv) ANTI-SENSE: NO (v) FRAGMENT TYPE: C-terminal (xi) SEQUENCE DESCRIPTION: SEQ ID NO: 8:

Glu Ser Lys Phe Arg Asn Trp Ser Ala Gly Tyr Ala Asp Phe Asp Arg
1               5                  10                 15

Gly Ala Tyr Val Ile Thr Phe Ile Pro Lys Ser Trp Asn Thr Ala Pro
            20                  25                 30

Ala Glu Val Lys Gln Gly Trp Pro
        35                  40

(2) INFORMATION FOR SEQ ID NO:9:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

CCTCATTCTG CAGCAGCGGC GGCAGCCGAC GAAAGGGTCA CCCCTCCCGC C        51

(2) INFORMATION FOR SEQ ID NO:10:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:10:

GCGCGAAGCT TCACGACCAG CCCTGCTTTA CCTCGGCGGG GGC        43